US009549994B2

(12) United States Patent
Gupta et al.

(10) Patent No.: US 9,549,994 B2
(45) Date of Patent: Jan. 24, 2017

(54) COMPOSITIONS OF NICARDIPINE AND SULFOALKYLATED β-CYCLODEXTRIN

(71) Applicant: EKR Therapeutics, Inc., Cary, NC (US)

(72) Inventors: Supriya Gupta, Sunnyvale, CA (US); Yanli Mi, San Mateo, CA (US); Camellia Zamiri, Fremont, CA (US)

(73) Assignee: EKR Therapeutics, Inc., Cedar Knolls, NJ (US)

( * ) Notice: Subject to any disclaimer, the term of this patent is extended or adjusted under 35 U.S.C. 154(b) by 0 days.

(21) Appl. No.: 14/030,692

(22) Filed: Sep. 18, 2013

(65) Prior Publication Data
US 2014/0206643 A1    Jul. 24, 2014

Related U.S. Application Data

(63) Continuation of application No. 13/457,946, filed on Apr. 27, 2012, now abandoned, which is a
(Continued)

(51) Int. Cl.
*A61K 31/455* (2006.01)
*A61K 47/48* (2006.01)
(Continued)

(52) U.S. Cl.
CPC ....... *A61K 47/48969* (2013.01); *A61K 9/0019* (2013.01); *A61K 31/4422* (2013.01); *A61K 31/455* (2013.01); *A61K 47/10* (2013.01); *A61K 47/12* (2013.01); *A61K 47/14* (2013.01); *A61K 47/26* (2013.01); *A61K 47/40* (2013.01); *B82Y 5/00* (2013.01); *C08B 37/0015* (2013.01); *C08L 5/16* (2013.01)

(58) Field of Classification Search
CPC .................. A61K 31/455; A61K 47/48969
See application file for complete search history.

(56) References Cited

U.S. PATENT DOCUMENTS 3,985,758 A   10/1976   Murakami
4,711,902 A   12/1987   Serno
(Continued)

FOREIGN PATENT DOCUMENTS

EP    0149475    7/1985
EP    0162705    11/1985
(Continued)

OTHER PUBLICATIONS

Tanaka et al.; "Separation of Neutral and Basic Enantiomers by Cyclodextrin Electrokinetic Chromatography Using Anionic Cyclodextrin Derivatives and Chiral Pseudo-Stationary Phases"; 1996; J. High Resol. Chromatogr.; 19: 421-433.*
(Continued)

*Primary Examiner* — Timothy Thomas
(74) *Attorney, Agent, or Firm* — Lowenstein Sandler LLP

(57) ABSTRACT

Compositions of an inclusion complex of nicardipine or a pharmaceutically acceptable salt thereof and a sulfoalkylated β-cyclodextrin. The compositions being formulated for parenteral bolus administration to a human subject. The compositions being useful in the treatment of cardiovascular and cerebrovascular disorders.

10 Claims, 6 Drawing Sheets

Related U.S. Application Data continuation of application No. 12/572,130, filed on Oct. 1, 2009, now abandoned, which is a continuation of application No. 11/737,067, filed on Apr. 18, 2007, now abandoned.

(60) Provisional application No. 60/793,074, filed on Apr. 18, 2006.

(51) Int. Cl.

| | | |
|---|---|---|
| A61K 9/00 | (2006.01) | |
| A61K 31/4422 | (2006.01) | |
| A61K 47/10 | (2006.01) | |
| A61K 47/12 | (2006.01) | |
| A61K 47/14 | (2006.01) | |
| A61K 47/26 | (2006.01) | |
| A61K 47/40 | (2006.01) | |
| C08B 37/16 | (2006.01) | |
| C08L 5/16 | (2006.01) | |
| B82Y 5/00 | (2011.01) | |

(56) References Cited

U.S. PATENT DOCUMENTS

| | | | |
|---|---|---|---|
| 4,880,823 A | 11/1989 | Ogawa et al. | |
| 4,940,556 A | 7/1990 | MacFarlane | |
| 5,079,237 A | 1/1992 | Husu | |
| 5,164,405 A | 11/1992 | McFarlane et al. | |
| 5,198,226 A | 3/1993 | MacFarlane | |
| RE34,618 E | 5/1994 | Ogawa | |
| 5,376,645 A * | 12/1994 | Stella et al. | 514/58 |
| 5,519,012 A | 5/1996 | Fercej-Temeljotov | |
| 5,904,929 A | 5/1999 | Uekama | |
| 6,595,926 B1 | 7/2003 | Laragh | |
| 2007/0112041 A1 | 5/2007 | Bhowmick et al. | |
| 2007/0249689 A1 | 10/2007 | Duncan et al. | |

FOREIGN PATENT DOCUMENTS

| | | |
|---|---|---|
| EP | 0324982 | 7/1989 |
| GB | 2228412 | 8/1990 |
| WO | 9111172 | 8/1991 |
| WO | 2007121483 | 10/2007 |

OTHER PUBLICATIONS

Sun et al.; CN 1326731 A; 2001; English machine translation.*
McIntosh, et al.; "In Vitro and In Vivo Evaluation of a Sulfobutyl Ether β-Cyclodextrin Enabled Etomidate Formulation"; 2004; Journal of Pharmaceutical Sciences; 93(10): 2585-2594.*
Fernandes et al.; "Physicochemical characterization and in vitro dissolution behavior of nicardipine—cyclodextrins inclusion compounds"; 2002; European Journal of Pharmaceutical Sciences 15: 79-88.*
Atlee et al., "The use of esmolol, nicardipine, or their combination to blunt hemodynamic changes after laryngoscopy and tracheal intubation," Anesth Analg, vol. 90:280-285 (Feb. 2000).
Aya et al., "Intravenous nicardipine for severe hypertension in pre-eclampsia—effects of an acute treatment on mother and foetus," Intensive Care Med., vol. 25(11):1277-1281 (Nov. 1999).
Bernard et al., "Long-term hypotensive technique with nicardipine and nitroprusside during isoflurane anesthesia for spinal surgery," Anesth Analg., vol. 75(2):179-185 (Aug. 1992).
Chen et al., "The comparative potentcy of intravenous nicardipine and verapamil on the cardiovascular response to tracheal intubation," Acta Anaesthesiol Sin., vol. 34(4):197-202 (Dec. 1996).
Cheung et al., "Acute pharmacokinetic and hemodynamic effects of intravenous bolus dosing of nicardipine," Am Heart J., vol. 119(2 Pt 2):438-442 (Feb. 1990).
Cheung et al., "Nicardipine intravenous bolus dosing for acutely decreasing arterial blood pressure during general anesthesia for cardiac operations: pharmacokinetics, pharmacodynamics, and associated effects on left ventricular function," Anesth Analg, vol. 89:1116-1123 (Nov. 1999).
Colson et al., "Haemodynamic heterogeneity and treatment with the calcium channel blocker nicardipine during phaeochromocytoma surgery," Acta Anaesthesiol Scand., vol. 42(9):1114-1119 (Oct. 1998).
Elatrous et al., "Short-term treatment of severe hypertention of pregnancy: prospective comparison of nicardipine and labetalol," Intensive Care Med., vol. 28(9):1281-1286 (Jul. 26, 2002).
Endoh et al., "Effects of nicardipine-, nitroglycerin-, and prostaglandin E1-induced hypotension on human cerebrovascular carbon dioxide reactivity during propofol-fentanyl anesthesia," J Clin Anesth, vol. 11(7):545-549 (Nov. 1999).
European Search Report on Application No. 07760862.8 dated Apr. 15, 2010.
Flynn et al., "Intravenous nicardipine for treatment of severe hypertension in children," J Pediatr., vol. 139(1):38-43 (Jul. 2001).
International Search Report for PCT/US2007/009549, published Jan. 3, 2008.
International Preliminary Report on Patentability for PCT/US2007/009549, dated Oct. 22, 2008.
International Preliminary Report on Patentability for PCT/US2007/066897, dated Jan. 13, 2009.
International Search Report for PCT/US2007/066897, published Feb. 19, 2009.
Kwak et al., "Comparison of the effects of nicardipine and sodium nitroprusside for control of increased blood pressure after coronary artery bypass graft surgery," J Int Med Res, vol. 32:342-350 (Jul.-Aug. 2004).
Pol Biopharma, Inc.; "Cardene IV (nicardipine hydrochloride)," Product Insert, Jan. 2006, USA.
Song et al., "Optimal dose of nicardipine for maintenance of hemodynamic stability after tracheal intubation and skin incision," Anesth Analg, vol. 85:1247-1251 (Dec. 1997).
Sweet Ana et al., "Solubility principles and practices for parenteral drug dosage form development." PDA J. of Pharma. Sci. and Technology, 50(5): pp. 330-341, 1996.
Vincent et al., "Intravenous nicardipine in the treatment of postoperative arterial hypertension," J Cardiothorac Vasc Anesth, vol. 11 (2):160-164 (Apr. 1997).
Written Opinion of the International Searching Authority for PCT/US2007/066897, mailed Nov. 24, 2008.
Yang et al., "Nicardipine versus nitroprusside infusion as antihypertensive therapy in hypertensive emergencies," J. Int Med Research, vol. 32(2):118-123 (Mar.-Apr. 2004).
Zhang et al., "The use of nicardipine for electroconvulsive therapy: a dose-ranging study," Anesth Analg, vol. 100:378-381 (Feb. 2005).

* cited by examiner

COMPOSITIONS OF NICARDIPINE AND SULFOALKYLATED β-CYCLODEXTRIN

CROSS-REFERENCES TO RELATED APPLICATIONS

This application is a continuation of U.S. patent application Ser. No. 13/457,946, filed on Apr. 27, 2012; which is a continuation of U.S. patent application Ser. No. 12/572,130, filed Oct. 1, 2009; which is a continuation of U.S. patent application Ser. No. 11/737,067, filed Apr. 18, 2007, and claims priority benefit under 35 U.S.C. §119(e) to U.S. Provisional Application Ser. No. 60/793,074, filed Apr. 18, 2006, all of which are incorporated by reference herein in their entireties.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND

Dihydropyridine calcium channel blockers are useful in the treatment of cardiovascular and cerebrovascular disorders. These agents act by inhibiting calcium uptake into vascular smooth muscle cells and mobilizing calcium from their intracellular stores. The vascular smooth muscle relaxes leading to vasodilation, decreased peripheral vascular resistance and decreased blood pressure. Examples of dihydropyridine calcium channel blockers include: amlodipine (NORVASC®), bepridil, diltiazem (CARDIZEM®), felodipine (PLENDIL®), isradipine (DYNACIRC®), mibefradil, nicardipine hydrochloride (CARDENE®), nifedipine (ADALAT® and PROCARDIA®), nimodipine (NIMOTOP®), nisoldipine (SULAR®), verapamil (CALAN®, ISOPTIN® and VERELAN®) and nilvadipine.

Nicardipine has a number of pharmaceutically acceptable salts, including the hydrochloride salt (e.g., IUPAC chemical name (±)-2-(benzyl-methyl amino)ethyl methyl 1,4-dihydro-2,6-dimethyl-4-(m-nitrophenyl)-3,5-pyridinedicarboxylate monohydrochloride). The preparation and use of nicardipine hydrochloride are described in U.S. Pat. No. 3,985,758. CARDENE® (nicardopine hydrochloride) is sold commercially in several forms. For example, nicardipine hydrochloride is available as an immediate release oral capsule, an extended release oral capsule, and as a concentrated preparation provided as an ampule (i.e., CARDENE® I.V.) that is greatly diluted into a pharmaceutically acceptable diluent before administration to a patient. CARDENE® I.V. is indicated for the short-term treatment of hypertension when oral therapy is not feasible or not desirable (see, the product insert for CARDENE® I.V.).

"Injectable" formulations of nicardipine have been described. For example, U.S. Reissue Pat. No. RE. 34,618, a reissue of U.S. Pat. No. 4,880,823, describes an injectable composition of nicardipine hydrochloride that is stored in a light resistant brown ampule and avoids the use of sodium chloride, particularly as a tonicity agent, in the formulation. U.S. Pat. No. 5,164,405 describes a buffered pharmaceutical composition containing nicardipine that is designed for parenteral administration. This composition is also stored in an ampule. A drawback of both these ampule formulations is that they must be greatly diluted into a pharmaceutically acceptable diluent before administration to a patient.

While nicardipine exists in oral and injectable forms, a bolus formulation of nicardipine has not been approved by the FDA. Nevertheless, nicardipine is administered off-label as a bolus injection. Administration requires dilution of the concentrated ampul formulation. See for example, Deanna Cheung, et al., *Am Heart J.*, vol. 119, pp. 438-442 (1990); Albert Cheung et al., *Anesth Analg*, vol. 89, pp. 1116-1123 (1999); (author), *Anesth Analg*, vol. 85, pp. 1247-1251 (1997); Yunan Zhang et al., *Anesth Analg*, vol. 100, pp. 378-381 (2005); John L Atlee et al., *Anesth Analg*, vol. 90, pp. 280-285 (2000); H J Yang et al., *J. Int Med Research*, (cite); Jean-Louis Vincent et al., *J. CardiothoracicVasc Anesth*, vol. 11, pp. 160-164 (1997); Chia-Chen Chen, et al., *Acta Anaesthesiol Sin*, vol. 34, pp. 197-202 (1996); Y L Kwak, et al., *J. Int Med Research*, vol. 32, pp. 342-350 (2004); P Colson et al., *Acta Anaesth Scand*, vol. 42, pp. 1114-1119 (1998); Jean-Marc Bernard et al., *Anesth Analg*, vol. 75, pp. 179-85 (1992); Hiroshi Endoh et al., *J. Clin Anesthesia* vol. 11, pp. 545-549 (1999); A G M Aya et al., *Intensive Care Med*, vol. 25, pp. 1277-1281 (1999); S. Elatrous et al., *Intensive Care Med*, vol. 28, pp. 1282-1286 (2002); Joseph Flynn et al., *J. Pediatr*, vol. 139, pp. 38-43 (2001); and other references.

Pharmaceutical compositions that are supplied in ampules have several important drawbacks. For example, these ampule formulations must be diluted into a pharmaceutically acceptable diluent prior to use. Therefore, they are not immediately available for use, such as in an emergency setting. Ampule compositions that must be diluted before use introduce the possibility of dosing errors in making the dilution; and safety hazards associated with the use of glass ampules. In addition, according to guidelines for administration of admixed (premixed) products in hospital settings, admixed solutions should be used within 24 hours in order to minimize the risk of microbial contamination. See The United States Pharmacopeia, vol. 1, p. 349 (2007). In addition to the concerns generally associated with off-label use of ampule formulations, CARDENE® I.V. (nicardipine hydrochloride ampule) presents two additional challenges. First, the pH of the diluted solution varies widely because the concentrated ampule solution can be diluted into various diluents, as described in the product insert for CARDENE® I.V. Second, as shown in the product insert for CARDENE® I.V., the diluted solution is only stable for 24 hours at room temperature. Therefore, the diluted solution must be used relatively quickly or it will expire.

To minimize the possibility of hemolysis, precipitation, phelebitis and pain, drugs which are directly injected into the circulatory system need to have little to no precipitate formed during storage, and upon contact and subsequent dilution in blood following administration (see., e.g., Yalkowsky, et al., 1998, J. Pharmaceutical Sciences, 87(7): 787-796). Nicardipine is a weak organic base, having a pKa of 7.2, and dissolves poorly in water-based formulations, especially at physiological pH. To avoid precipitation of nicardipine when administered in a more concentrated form, its poor aqueous solubility must be overcome. Thus, there is a long-felt need for a low volume, stable aqueous pharmaceutical formulation of nicardipine which can provide a therapeutically effective dosage and which does not appreciably degrade upon storage or precipitate when parenterally administered in a more concentrated, lower volume formulation.

The compositions provided herein address these and other needs by providing a relatively low volume, pre-mixed, ready-to-use, injectable formulation of nicardipine that is stable enough for clinical use, and yet provides a suitable nicardipine concentration for immediate use, without dilution, by parenteral injection.

BRIEF SUMMARY

To meet these and other needs, provided herein are pharmaceutical compositions of nicardipine for direct bolus parenteral administration to a subject and methods of using the compositions to prevent or treat acute elevations of blood pressure in a subject. The compositions can be administered by parenteral routes, including, subcutaneous, intramuscular, and intravenous routes, to a patient.

Accordingly a first aspect provides pharmaceutical compositions of nicardipine for direct bolus intravenous administration to a human subject. In this aspect, the pharmaceutical composition comprises 0.25 mg to 5.0 mg/ml, inclusive of nicardipine (as calculated for either nicardipine base or its hydrochloride salt) in an aqueous formulation having one or more buffering agent(s) each in a concentration from 0.1 mM to 100 mM, and a pH from about 3.5 to 5.5, inclusive, and one or more additional pharmaceutically acceptable excipients or carriers. In some embodiments, the buffering agent(s) can be any one or more salts and acids of citrate, malate, formate, succinate, acetate, propionate, histidine, carbonate, tartrate, phosphate, or 2-(N-morpholino)ethanesulfonic acid (MES). Optionally, the composition comprises a tonicity adjusting agent and/or a co-solvent. Suitable tonicity adjusting agents include but are not limited to, dextrose or sodium chloride. Suitable co-solvents include but are not limited to, polyhydric alcohols (e.g., sorbitol, mannitol, xylitol), glycols (e.g., propylene glycol and polyethylene glycol), and ethanol in a concentration range varying from 0.1 to 25% w/v. Typically, the compositions are provided as low volume, pre-mixed, ready-to-use, bolus injectable, aqueous pharmaceutical compositions. Alternatively, the compositions may be lyophilized and reconstituted in water, saline or a pharmaceutically acceptable aqueous carrier to provide the compositions for use as a bolus injection.

In some further embodiments, the use of nicardipine or a pharmaceutically acceptable salt thereof in the manufacture of the above compositions for the prevention or treatment of acute elevations of blood pressure in a human subject in need thereof are provided.

The second aspect provides pharmaceutical compositions formulated for bolus direct intravenous administration to a human subject which comprises an inclusion complex of nicardipine and/or a pharmaceutically acceptable salt thereof with a sulfoalkylated β-cyclodextrin. Typically, the concentration of the sulfoakylated β-cyclodextrin in the formulation is from 0.1% to 25% (w/v), inclusive. The pharmaceutical composition comprises 0.25 mg to 5.0 mg/ml, inclusive of nicardipine (as calculated for either nicardipine base or its hydrochloride salt) in an aqueous formulation having one or more buffering agent(s) each in a concentration from 0.1 mM to 100 mM, and a pH from about 3.5 to 7.5, inclusive, and one or more additional pharmaceutically acceptable excipients or carriers. In some embodiments, the buffering agent(s) can be any one or more of an acid or salt of citrate, malate, formate, succinate, acetate, propionate, histidine, carbonate, phosphate, tartrate, or MES. Optionally, the composition comprises a tonicity adjusting agent and/or a co-solvent. Suitable tonicity adjusting agents for use in the compositions provided herein include, but are not limited to, dextrose or sodium chloride. Suitable co-solvents for use in the compositions provided herein include, but are not limited to, polyhydric alcohols (e.g., sorbitol, mannitol, xylitol), glycols (e.g., propylene glycol and polyethylene glycol), and ethanol, in a concentration range varying from 0.1 to 25% w/v. Typically, the compositions are provided as low volume, pre-mixed, ready-to-use, bolus injectable, aqueous pharmaceutical compositions. Alternatively, the compositions may be lyophilized and reconstituted in water, saline, or a pharmaceutically acceptable aqueous carrier to provide the compositions for use as a bolus injection.

In some further embodiments, the use of nicardipine and sulfoalkylated β-cyclodextrin derivatives in the manufacture of the above compositions for the prevention or treatment of acute elevations of blood pressure in a human subject in need thereof are provided.

The pharmaceutical compositions in either of the above aspects can be packaged for use in a variety of containers, such as syringes, ampules, or vials. Typically, the compositions are packaged with materials that protect nicardipine from light.

Examples of pharmaceutically acceptable salts of nicardipine are hydrochlorides, sulfates, phosphates, acetates, fumarates, maleates and tartrates. In some embodiments, the pharmaceutically acceptable salt of nicardipine is nicardipine hydrochloride.

In a third aspect, are provided methods of preventing, or treating acute elevations of blood pressure in a human subject in need thereof by intravenously administering a bolus pharmaceutical composition as described above to the subject. The subjects may be volume-restricted due to any number of existing medical conditions, such as, edema, renal failure, ascites, cerebral edema, or other fluid overload, congestive heart failure, liver failure, or a CNS injury. The dosage can be administered over varying lengths of time and is generally administered over a period of less than 30 seconds, including from about 5 seconds to 30 seconds. In some embodiments, the subject has an elevated blood pressure with a systolic value equal to or above 150 mmHg. In other embodiments, the subject has an elevated blood pressure with a diastolic value equal to or above 90 mmHg. Dosages can be individualized depending upon the severity of hypertension and the response of the individual patient during dosing.

In a fourth aspect, are provided methods for inducing hypotension during surgical procedures in a human subject in need thereof by intravenously administering a bolus formulation as described above to the subject.

DETAILED DESCRIPTION

Figure 1:
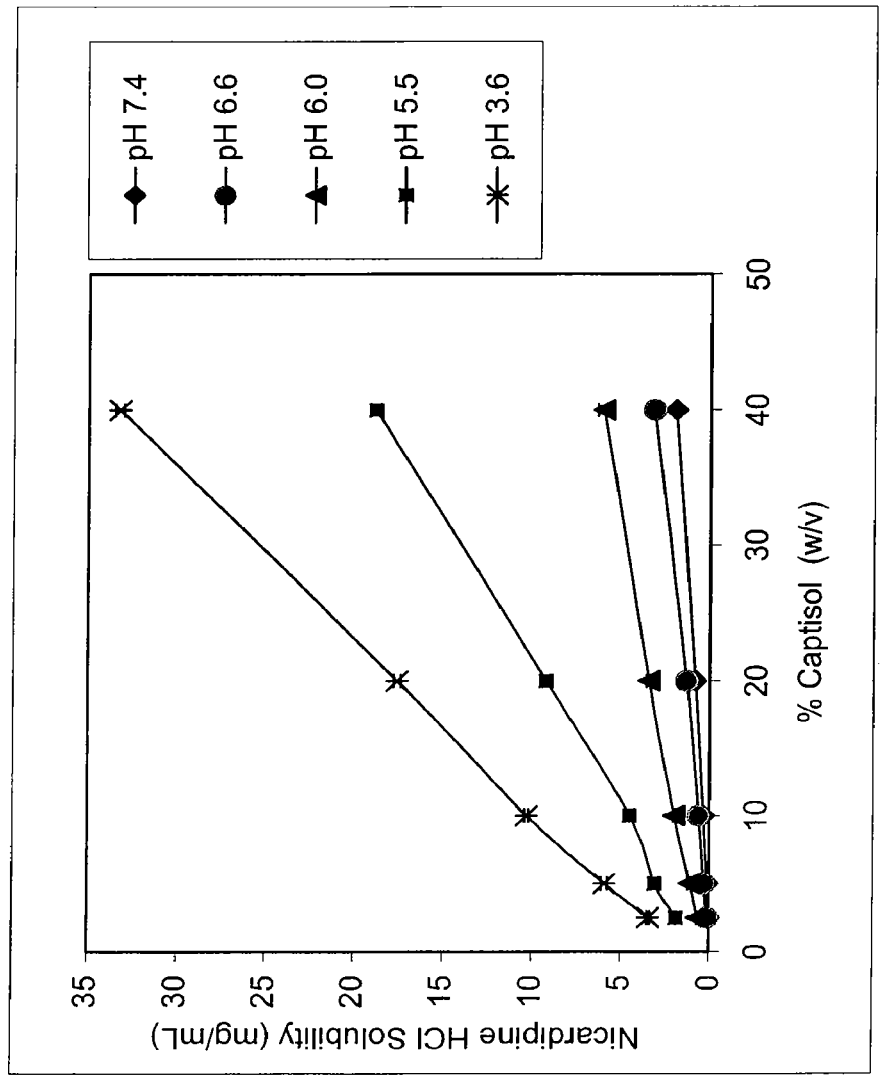
FIG. 1. Phase-solubility study to evaluate complexation of nicardipine HCl and CAPTISOL® (sulphobutylether β-cyclodextrin) as a function of pH.

Provided herein are pharmaceutical compositions of nicardipine which provide a therapeutic amount of the drug in a low volume for administration as an intravenous bolus. The provided formulations of nicardipine are stable upon storage and do not appreciably precipitate out when injected intravenously into a human subject. The bolus form of the composition is especially useful for the treatment of acute elevations in blood pressure when oral administration is not practicable because of the need for rapid blood pressure control or because oral administration itself is not suitable.

Nicardipine and its pharmaceutically acceptable salts, their preparation, and their use are known in the art. For example, they are disclosed in, among other references, U.S. Pat. No. 3,985,758, which is incorporated herein by reference in its entirety. Examples of pharmaceutically acceptable salts of nicardipine include hydrochlorides, sulfates, phosphates, acetates, fumarates, maleates and tartrates. The preferred pharmaceutically acceptable salt of nicardipine is nicardipine hydrochloride. The pharmaceutical compositions comprise 0.25 mg/ml to 5.0 mg/ml nicardipine or a pharmaceutically acceptable salt thereof. In one embodiment, the concentration is 0.25 to 1.0 mg/ml. The compositions can optionally include complexing agents such as cyclodextrins. In some embodiments, the compositions comprise one or more buffers. When expressed as mg/ml, the concentration of nicardipine is with respect to an amount of the nicardipine base which is the molar equivalent to that provided by nicardipine hydrochloride in the recited amount.

Definitions

It is noted here that as used in this specification and the appended claims, the singular forms "a," "an," and "the" include plural reference unless the context clearly dictates otherwise.

Compounds for use in the compositions described herein that may contain one or more asymmetric centers can thus occur as racemates and racemic mixtures, single enantiomers. The compositions are meant to comprehend all isomeric forms of such compounds.

All recited ranges are inclusive of the boundary values unless indicated otherwise. Accordingly, a pH of 4.0 to 5.0 includes pH's of 4.0 and 5.0, as well as various increments between, e.g., 4.1, 4.2, 4.3, 4.4, 4.5, 4.6, 4.7, 4.8, 4.9, and 5.0.

Where concentrations are given in units of percent, the percent is weight to volume (w/v) unless otherwise indicated. A 1% solution would have 1 g of solute dissolved in a final volume of 100 ml of solution.

The term "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients described herein. A pharmaceutical composition generally comprises a therapeutically effective amount of nicardipine, one or more buffering agents, and other ingredients as described herein.

A "therapeutically effective amount" is an amount of an agent sufficient to treat or prevent acute elevations in blood pressure or induce hypotension when administered alone or as one of multiple dosages to a subject. The "therapeutically effective amount" will vary depending on the formulation, the severity of the blood pressure elevation, the age, general health condition, and weight of the subject to be treated.

The term "pre-mixed", as used herein, means a pharmaceutical composition that is already mixed from the point of pre-sale packaging and/or manufacture and does not require reconstitution or dilution before administration to a subject.

The term "stable", as used herein, means remaining in a state or condition that is suitable for administration to a patient and without undergoing a substantial change in the potency of the active agent in the formulation over the specified time period. In some embodiments, compositions are stable when maintained at room temperature for at least 6 months, usually at least 12 months, and generally for at least 18 or 24 months. The compositions are also preferably stable over more extended periods of time when stored at 2-8° C. A substantial change in potency is one which decreases the drug concentration by more than 15%, from the target concentration for the specified period of time. Unless indicated otherwise, a stable composition is one which retains at least 85% of the original amount of the nicardipine in that state (e.g., not precipitated, degraded or adsorbed to the container) for a period of at least six months.

The carriers and excipients and other components of the pharmaceutical compositions must be "pharmaceutically acceptable" in the sense of being compatible with the other ingredients of the formulation and not deleterious to the recipient thereof. Accordingly, the term "pharmaceutically acceptable salt" references salt forms of the active compounds which are prepared with counter ions which are non-toxic under the conditions of use and are compatible with a stable formulation. For compounds which contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. Salts derived from pharmaceutically acceptable organic nontoxic bases include salts of primary, secondary, and tertiary amines, substituted amines including naturally occurring substituted amines, cyclic amines, ethanolamine, 2-diethylaminoethanol, lysine, arginine, and histidine.

For compounds which contain relatively basic functionalities, acid addition salts can be obtained by contacting the neutral form of such compounds with a sufficient amount of the desired base, either neat or in a suitable inert solvent. Examples of "pharmaceutically acceptable acid addition salts" (i.e., salts retaining the biological effectiveness and properties of the free bases and which are not biologically or otherwise undesirable), can be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like).

The term "pharmaceutically acceptable carrier or excipient" means a carrier or excipient that is useful in preparing a pharmaceutical composition that has an acceptable side-effect profile and serves to provide a medium for the storage or administration of the active component(s) under the conditions of administration for which the composition is formulated or used. The carrier or excipient is compatible with the other ingredients of the formulation and not deleterious to the recipient thereof. A "pharmaceutically acceptable carrier or excipient" as used in the specification and claims includes both one and than one such carrier or excipient. Pharmaceutically acceptable carriers are determined in part by the particular composition being administered, as well as by the particular method used to administer the composition. There are a wide variety of suitable formulations of pharmaceutical compositions of the present invention (see, e.g., *Remington's Pharmaceutical Sciences*, 20$^{th}$ ed., 2003, supra).

"Tonicity adjusting agents" are agents used to modify the osmolality of a formulation to bring it closer to the osmotic pressure of body fluids such as blood or plasma. Provided that the compositions are physiologically compatible, the compositions do not require any particular osmolality. Thus, the compositions can be hypotonic, isotonic, or hypertonic. Typically, the pharmaceutical compositions have an osmolality between about 250 to 350 mOsm/kg. The tonicity of the pharmaceutical compositions can be adjusted by adjusting the concentration of any one or more of a tonicity agent, a co-solvent, complexing agent, buffering agent, or excipient. Suitable tonicity adjusting agents include, but are not limited to, anhydrous and hydrous forms of NaCl, dextrose, sucrose, xylitol, fructose, glycerol, sorbitol, mannitol, KCl, $CaCl_2$, and $MgCl_2$.

"Buffering agents" are agents used to control the pH of a formulation. A variety of buffering agents are suitable and may be used alone or together in the composition. Suitable buffering agents include, but are not limited to, acids and salts of acetate, glutamate, citrate, tartrate, benzoate, ascorbic acid, lactate, amino acids, gluconate, succinate, MES, and phosphate. The buffering agent can be in a concentration from 0.1 to 100 mM, inclusive, 0.1 to 0.5 mM, 0.5 to 1 mM, 1 to 5 mM, 5 to 20 mM, inclusive, 5 to 50 mM, inclusive, or 50-100 mM inclusive.

The pH can be adjusted to the recited pH range or target pH by the addition of an acid or acidic salt (e.g., HCl, ascorbic acid, phosphoric acid), or base or basic salt, as appropriate. For instance, the pH may be adjusted with a base such as an alkali metal hydroxide such as NaOH, KOH, or LiOH, a phosphate, or an alkaline earth metal hydroxide, such as $Mg(OH)_2$ or $Ca(OH)_2$, or a carbonate. The buffering agent may be the acid or base form of the species which gives rise to the salt of the nicardipine.

A "co-solvent" is a solvent which is added to the aqueous formulation in a weight amount which is less than that of water and assists in the solubilization of the nicardipine or inclusion complex of nicardipine and the sulfoalkylated β-cyclodextrin. Co-solvents, for instance, can be selected from the group consisting of polyhydric alcohols (e.g., sorbitol, mannitol, xylitol), glycols (e.g., propylene glycol and polyethylene glycol) and ethanol. Typically, the co-solvent is in a concentration from 0.1% to 25%.

Pharmaceutical Compositions

A. Pharmaceutical Compositions Comprising Buffering Agents

Pharmaceutical compositions of nicardipine for direct intravenous administration to a human subject are provided. The nicardipine can be present as a pharmaceutically acceptable salt (e.g., a hydrochloride, chloride, sulfate, phosphate, succinate, acetate, fumarate, maleate, or tartarate salt. In some embodiments, the nicardipine concentration is in a range from 0.3 mg/ml to 0.7 mg/ml; 0.4 mg/ml to 0.6 mg/ml; or 0.5 mg/ml. In some embodiments, the nicardipine concentration is from 1.0 mg/ml to 0.9 mg/ml, from 0.9 mg/ml to 0.8 mg/ml, from 0.8 mg/ml to 0.7 mg/ml, from 0.7 mg/ml to 0.6 mg/ml, from 0.6 mg/ml to 0.5 mg/ml, from 0.5 mg/ml to 0.4 mg/ml, from 0.4 mg/ml to 0.3 mg/ml, 0.3 mg/ml to 0.25 mg/mL In a first aspect, formulations lacking CAPTISOL® (sulphobutylether β-cyclodextrin) are contemplated. In this aspect, the pharmaceutical composition comprises 0.25 to 5.0 mg/ml, inclusive, of nicardipine (as calculated for either the nicardipine base or its hydrochloride salt). In one embodiment, the composition comprises 0.25-1.0 mg/ml nicardipine. In one embodiment, the composition comprises 0.5 mg/mi nicardipine.

The compositions are in an aqueous formulation having one or more buffering agent(s) each in a concentration from 0.1 mM to 100 mM, and a pH from about 3.5 to 5.5, inclusive. For example, in some embodiments, the composition comprises a buffering agent from 0.5 mM to 50 mM in concentration and a pH more than 3.5 but less than 5.0. In some embodiments, the buffering agent(s) can be any one or more of an acid or salt of citrate, malate, formate, succinate, acetate, propionate, histidine, carbonate, tartrate. phosphate, or MES. In some embodiments, the buffer is a single buffer selected from the group consisting of acetate, citrate, succinate, and phosphate. In some embodiments, the compositions comprise two, three, four, or more different buffering agents. For example, in some embodiments, the compositions comprise two buffering agents, selected from the group consisting of acetate and citrate; acetate and phosphate; acetate and succinate; citrate and phosphate; citrate and succinate; and succinate and phosphate. In other embodiments, the compositions comprise three or more buffering agents selected from the group consisting of acetate, phosphate and succinate; citrate, phosphate and acetate; succinate, phosphate and citrate; and citrate, acetate and succinate buffering agents.

Optionally, the compositions can comprise tonicity adjusting agents and/or co-solvents. In some embodiments, the tonicity adjusting agent is dextrose or sodium chloride. In some embodiments, the co-solvent is polyhydric alcohols (e.g., sorbitol, mannitol, xylitol), glycols (e.g., propylene glycol and polyethylene glycol), and ethanol, in a concentration range varying from 0.1 to 25% w/v. In other embodiments, the cosolvent concentration is 0.1 to 10% w/v. Typically, the compositions are provided as low volume, pre-mixed, ready-to-use, injectable, bolus aqueous pharmaceutical compositions.

In some embodiments, the formulations comprise (a) nicardipine or a pharmaceutically acceptable salt thereof, (e.g., nicardipine hydrochloride), (b) at least one buffering agent; (c) a tonicity agent; and (d) optionally a co-solvent, in which the pH of the composition is between 3.5 and 5.5. Exemplary formulations are illustrated in Table 1.

TABLE 1

| Nicardipine HCl (mg/mL) | Buffer (mM) | Tonicity Adjusting Agents (%) w/v | Co-Solvent (%) w/v | pH range |
|---|---|---|---|---|
| 0.25-0.75 | 0.5-50 mM acetate | NaCl (0-1%) Dextrose (0-5%) | Sorbitol (0-5%) | 3.6-4.7 |
| 0.25-0.75 | 0.5-50 mM citrate | NaCl (0-1%) Dextrose (0-5%) | Sorbitol (0-5%) | 3.6-4.7 |
| 0.25-0.75 | 0.5-50 mM acetate, 0.5-50 mM citrate, 0.5-50 mM phosphate | NaCl (0-1%) Dextrose (0-5%) | Sorbitol (0-5%) | 3.6-4.7 |
| 0.25-0.75 | 0.5-50 mM acetate, 0.5-50 mM Succinate, 0.5-50 mM phosphate | NaCl (0-1%) Dextrose (0-5%) | Sorbitol (0-5%) | 3.6-4.7 |
| 0.25-0.75 | 0.5-50 mM citrate, 0.5-50 mM Succinate, 0.5-50 mM phosphate | NaCl (0-1%) Dextrose (0-5%) | Sorbitol (0-5%) | 3.6-4.7 |
| 0.25-0.75 | 0.5-50 mM citrate, 0.5-50 mM Succinate, 0.5-50 mM Acetate | NaCl (0-1%) Dextrose (0-5%) | Sorbitol (0-5%) | 3.6-4.7 |
| 0.25-0.75 | 0.5-50 mM acetate, 0.5-50 mM citrate | NaCl (0-1%) Dextrose (0-5%) | Sorbitol (0-5%) | 3.6-4.7 |
| 0.25-0.75 | 0.5-50 mM acetate, 0.5-50 mM phosphate | NaCl (0-1%) Dextrose (0-5%) | Sorbitol (0-5%) | 3.6-4.7 |
| 0.25-0.75 | 0.5-50 mM acetate, 0.5-50 mM succinate | NaCl (0-1%) Dextrose (0-5%) | Sorbitol (0-5%) | 3.6-4.7 |
| 0.25-0.75 | 0.5-50 mM citrate, 0.5-50 mM phosphate | NaCl (0-1%) Dextrose (0-5%) | Sorbitol (0-5%) | 3.6-4.7 |
| 0.25-0.75 | 0.5-50 mM citrate 0.5-50 mM succinate | NaCl (0-1%) Dextrose (0-5%) | Sorbitol (0-5%) | 3.6-4.7 |
| 0.25-0.75 | 0.5-50 mM succinate 0.5-50 mM phosphate | NaCl (0-1%) Dextrose (0-5%) | Sorbitol (0-5%) | 3.6-4.7 |

B. Pharmaceutical Compositions Comprising Complexing Agents

In the second aspect, pharmaceutical compositions are provided that are formulated for intravenous administration to a human subject and comprise an inclusion complex of nicardipine and/or a pharmaceutically acceptable salt thereof with a sulfoalkylated β-cyclodextrin. The nicardipine can be present as a pharmaceutically acceptable salt (e.g., a hydrochloride, chloride, sulfate, phosphate, succinate, acetate, fumarate, maleate, or tartarate salt. In some embodiments, the nicardipine concentration is in a range from 0.3 mg/ml to 0.7 mg/ml; 0.4 mg/ml to 0.6 mg/ml; or 0.5 mg/ml. In some embodiments, the nicardipine concentration is from 1.0 mg/ml to 0.9 mg/ml, from 0.9 mg/ml to 0.8 mg/ml, from 0.8 mg/ml to 0.7 mg/ml, from 0.7 mg/ml to 0.6 mg/ml, from 0.6 mg/ml to 0.5 mg/ml, from 0.5 mg/ml to 0.4 mg/ml, from 0.4 mg/ml to 0.3 mg/ml, 0.3 mg/mL to 0.25 mg/ml.

The sulfoalkyl ether cyclodextrin derivative(s) are sulfobutyl ether-β-cyclodextrins with an average degree of substitution between 1 and 7 of sulfobutyl ether groups per cyclodextrin molecule. Generally, highly substituted butylsulfonic or propylsulfonic acids are utilized in the compositions described herein because they cause less membrane disruption, as determined by red blood cell hemolysis studies. An example of a highly substituted bufylsulfonic acid that can be used in the formulations described herein is sulfobutyl ether β-cyclodextrin is commercially available as CAPTISOL® (with an average degree of substitution 7 of sulfobutyl ether groups per cyclodextrin molecule).

In other embodiments, U.S. Pat. No. 5,079,237 describes an inclusion complex of a drug with naturally occurring α-cyclodextrin, β-cyclodextrin or γ-cyclodextrin. U.S. Pat. No. 5,519,012 describes inclusion complexes of drugs with hydroxy-alkylated-β-cyclodextrins, such as 2-hydroxypropyl-β-cyclodextrin, 3-hydroxypropyl-β-cyclodextrin, 2-hydroxyethyl-β-cyclodextrin, and 2,3-dihydroxypropyl-β-cyclodextrin. U.S. Pat. No. 5,904,929 describes numerous drugs for trans-mucosal or transdermal administration in formulations with per-$C_{2-18}$ acylated cyclodextrins. The cyclodextrin may be an α, β or γ-cyclodextrin. U.S. Pat. Nos. 5,134,127 and 5,376,645 disclose sulfoalkyl ether cyclodextrin derivatives and their use as solubilizing agents for some water-insoluble drugs for oral, intranasal or parenteral administration as well as intravenous and intramuscular administration. Examples of sulfoalkyl ether cyclodextrin derivatives disclosed include the mono-sulfobutyl ether of β-cyclodextrin and the monosulfopropyl ether of β-cyclodextrin.

Typically, the concentration of the sulfoalkylated β-cyclodextrin in the formulation is from 0.1% to 25% (w/v), inclusive. In one embodiment, the concentration is from 0.5-10% w/v.

In this aspect, the pharmaceutical composition comprises 0.25 to 5 mg/ml, inclusive, of nicardipine (as calculated for either the nicardipine base or its hydrochloride salt). In one embodiment, the composition comprises 0.25-1 mg/ml nicardipine. In one embodiment, the composition comprises 0.5 mg/ml nicardipine.

The compositions are in aqueous formulations having one or more buffering agent(s), each in a concentration from 0.1 mM to 100 mM, and a pH from 3.5 to 7.5, inclusive. In some embodiments, the formulations comprise one or more buffering agents, each in a concentration from 0.5 mM to 50 mM and a pH more than 3.5 but less than or equal to 5.5. In some embodiments, the buffering agent(s) can be any one or more of an acid or salt of citrate, tartrate, malate, formate, succinate, acetate, propionate, histidine, carbonate, phosphate, or MES. In one embodiment, the buffer is selected from the group consisting of acetate, citrate, phosphate, and succinate. The composition can comprise one, two, three or more buffers as described above for the first aspect. For example, in some embodiments, the composition comprises two buffering agents, selected from the group consisting of acetate and citrate; acetate and phosphate; acetate and succinate; citrate and phosphate; citrate and succinate; and succinate and phosphate. In some embodiments, the composition comprises three or more buffering agents selected from the group consisting of acetate, phosphate and succinate; citrate, phosphate and acetate; succinate, phosphate and citrate; and citrate, acetate and succinate buffering agents.

Optionally, the composition comprises a tonicity adjusting agent and/or a co-solvent. In some embodiments, the tonicity adjusting agent is dextrose or sodium chloride. In some embodiments, suitable co-solvents include, but are not limited to polyhydric alcohols (e.g., sorbitol, mannitol, xylitol), glycols (e.g., propylene glycol and polyethylene glycol), and ethanol. In some embodiments, the co-solvent is sorbitol. Typically the concentration of the co-solvent varies from about 0.1 to 25% w/v. In some embodiments, the concentration of the co-solvent varies from 0.1 to 10% w/v.

Typically, the compositions are provided as low volume, pre-mixed, ready-to-use, injectable, bolus aqueous pharmaceutical compositions. Alternatively, the compositions may be lyophilized and reconstituted in water, saline, or a pharmaceutically acceptable aqueous carrier to provide the compositions.

Accordingly, provided herein are an injectable, aqueous pharmaceutical compositions comprising: (a) nicardipine or pharmaceutically acceptable salt thereof (e.g., nicardipine), (b) a complexing agent, and (c) optionally, at least one of a co-solvent and/or tonicity agent, (d) a buffering agent, in which the pH of the composition is between 3.5 and 7.5. Suitable buffering agents include at least one acid or salt of acetate, succinate, glutamate, citrate, tartrate, benzoate, lactate, histidine, gluconate and phosphate. Suitable cosolvents include polyhydric alcohols (e.g., sorbitol, mannitol, xylitol), glycols (e.g., propylene glycol and polyethylene glycol), and ethanol. Generally, the complexing agent comprises a cyclodextrin. In some embodiments, the cyclodextrin comprises at least one of 2-hydroxypropyl-β-cyclodextrin, α-cyclodextrin, and sulfobutylether-β-cyclodextrin. Suitable tonicity agents include sodium chloride and dextrose.

For example, in some embodiments, the composition comprises (a) nicardipine or pharmaceutically acceptable thereof (e.g., nicardipine hydrochloride), (b) a complexing agent, and (c) a buffering agent, in the pH of the composition is between 3.5 and 7.5. Exemplary formulations incorporating these agents are illustrated in TABLE 2.

TABLE 2

| Nicardipine HCl (mg/mL) | Buffer (mM) | Complexing Agent (%) w/v | Tonicity Adjusting Agents (%) w/v | Co-Solvent (%) w/v | PH range |
|---|---|---|---|---|---|
| 0.25-0.75 | 0.5-50 mM acetate | Sulfobutylether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM citrate | Sulfobutlyether β-cyclodextrin (0.5-10%) Or Hydroxypropyl βcyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM acetate, 0.5-50 mM citrate, 0.5-50 mM phosphate | Sulfobutlyether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM acetate, 0.5-50 mM succinate, 0.5-50 mM phosphate | Sulfobutlyether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM citrate, 0.5-50 mM succinate, 0.5-50 mM phosphate | Sulfobutlyether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM citrate, | Sulfobutlyether β-cyclodextrin | NaCl (0-1%) Dextrose (0-5%) | Sorbitol (0-5%) | 3.5-5.5 |

TABLE 2-continued

| Nicardipine HCl (mg/mL) | Buffer (mM) | Complexing Agent (%) w/v | Tonicity Adjusting Agents (%) w/v | Co-Solvent (%) w/v | PH range |
|---|---|---|---|---|---|
| | 0.5-50 mM succinate, 0.5-50 mM acetate | (0.5-10%) Or Hydroxypropyl β-cyclodextrin (0.5-10%) Or α-cyclodextrin (0.5-10%) | | | |
| 0.25-0.75 | 0.5-50 mM acetate, 0.5-50 mM citrate | Sulfobutlyether β-cyclodextrin (0.5-10%) Hydroxypropyl β-cyclodextrin (0.5-10%) α-cyclodextrin (0.5-10%) | NaCl (0-1%) Dextrose (0-5%) | Sorbitol (0-5%) | 3.5-5.5 |
| 0.25-0.75 | 0.5-50 mM acetate, 0.5-50 mM phosphate | Sulfobutlyether β-cyclodextrin (0.5-10%) Hydroxypropyl β-cyclodextrin (0.5-10%) α-cyclodextrin (0.5-10%) | NaCl (0-1%) Dextrose (0-5%) | Sorbitol (0-5%) | 3.5-5.5 |
| 0.25-0.75 | 0.5-50 mM acetate, 0.5-50 mM succinate | Sulfobutlyether β-cyclodextrin (0.5-10%) Hydroxypropyl β-cyclodextrin (0.5-10%) α-cyclodextrin (0.5-10%) | NaCl (0-1%) Dextrose (0-5%) | Sorbitol (0-5%) | 3.5-5.5 |
| 0.25-0.75 | 0.5-50 mM citrate, 0.5-50 mM phosphate | Sulfobutlyether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM citrate 0.5-50 mM succinate | Sulfobutlyether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |
| 0.25-0.75 | 0.5-50 mM succinate 0.5-50 mM phosphate | Sulfobutlyether β-cyclodextrin (0.5-10%) Or Hydroxypropyl β-cyclodextrin (0.5-10%) Or α-cyclodextrin (0.5-10%) | NaCl (0-1%) Dextrose (0-5%) | Sorbitol (0-5%) | 3.5-5.5 |

The compositions can comprise one or more additional pharmaceutically acceptable excipients or carriers.

In some embodiments, the pharmaceutical compositions are any as described in U.S. Provisional Application Ser. No. 60/793,084, filed Apr. 18, 2006, which is incorporated herein by reference.

Methods of Treatment

In a third aspect, the pharmaceutical compositions described above are used for the prevention or treatment of acute elevations of blood pressure in a human patient in need thereof. In some embodiments, the patients being treated may be volume-restricted due to a co-existing medical condition. Examples of medical conditions in which it would be advantageous to administer low volume formulations include, renal failure, ascites, cerebral edema, congestive heart failure, liver failure, or a CNS injury. Dosages can be individualized depending upon the severity of hypertension and the response of the individual patient during dosing.

Typically, the dosage is administered as a bolus dose over a period of less than thirty seconds or may be administered as a continuous infusion of a pre-mixed product. In some embodiments, the patient has an elevated blood pressure with a systolic equal to or greater than 150 mm Hg. In other embodiments, the subject has an elevated blood pressure with a diastolic value greater than or equal to 90 mm Hg.

In some embodiments, the pharmaceutical compositions can be used to prevent acute elevations of blood pressure associated with various medical procedures. Examples of medical procedures associated with acute elevations of blood pressure include, but are not limited to, electroconvulsive therapy (see, e.g., Avramov, et al., 1998, J. Clinical Anesthesia, 10:394-400), carotid endarterectomy (see, e.g., Dorman, et al., 2001, J. Clinical Anesthesia, 13:16-19, tracheal intubation (Song, et al., 2001, Anesth Analg., 85:1247-51) and skin incision (Song, et al., 2001, Anesth Analg., 85:1247-51).

In some embodiments, the pharmaceutical compositions can be used to treat acute elevations in blood pressure due to certain cardiovascular and cerebrovascular conditions. Examples of cardiovascular conditions that are associated with acute elevations of blood pressure include, but are not limited to, essential hypertension, angina, acute ischemia, systemic arterial hypertension, congestive heart failure, coronary artery disease, myocardial infarction, cardiac arrhythmias, cardiomyopathies and arteriosclerosis. Examples of cerebrovascular conditions are associated with acute elevations of blood pressure include, but are not limited to pulmonary hypertension, cerebral insufficiency and migraine headache. In other embodiments, the pharmaceutical compositions can be used to treat acute elevations in blood pressure due to kidney disorders.

In some embodiments, the pharmaceutical compositions can be used to induce hypotension during surgical procedures including, but not limited to cardiothoracic surgery, spinal surgeries and head and neck surgeries.

For bolus administration, the compositions are typically provided in a unit dose format and the unit dose provides a therapeutically effective amount of nicardipine in a unit dose or fill volume of from 0.5 to 10 ml, inclusive. For instance, the unit dose or fill volume may be 0.5 to 1.0 ml, 1.0 to 2 ml, 2 to 3 ml, 3 to 4 ml, 4 to 5 ml, 5 to 6 ml, 6 to 7 ml, 7 to 8 ml, 8 to 9 ml, and 9 to 10 ml.

The unit dose or fill volume may be provided in a pharmaceutically acceptable container, such as a vial or a syringe. In some embodiments, the container does not comprise polar polymers, e.g., polyvinylchloride. To shield the compositions from light, amber colored vials or syringes can be used, and/or the packaging can further include a light barrier. The light barrier can be an aluminum overpouch.

The methods of treatment relate to Applicant's findings that pharmaceutical compositions of nicardipine co-formulated with buffering agents and/or a sulfobutyl ether β-cyclodextrin reduce the potential for the nicardipine to precipitate at the site of injection, and stabilize the nicardipine during storage over specified ranges of pH values. The invention further relates to the Applicant's findings that the use of buffering agents with varying pKa's such that sufficient buffering capacity is obtained over the pH range from 3.5-7.5 can be effective in minimizing the potential for nicardipine to precipitate at the site of injection.

Figure 2A:
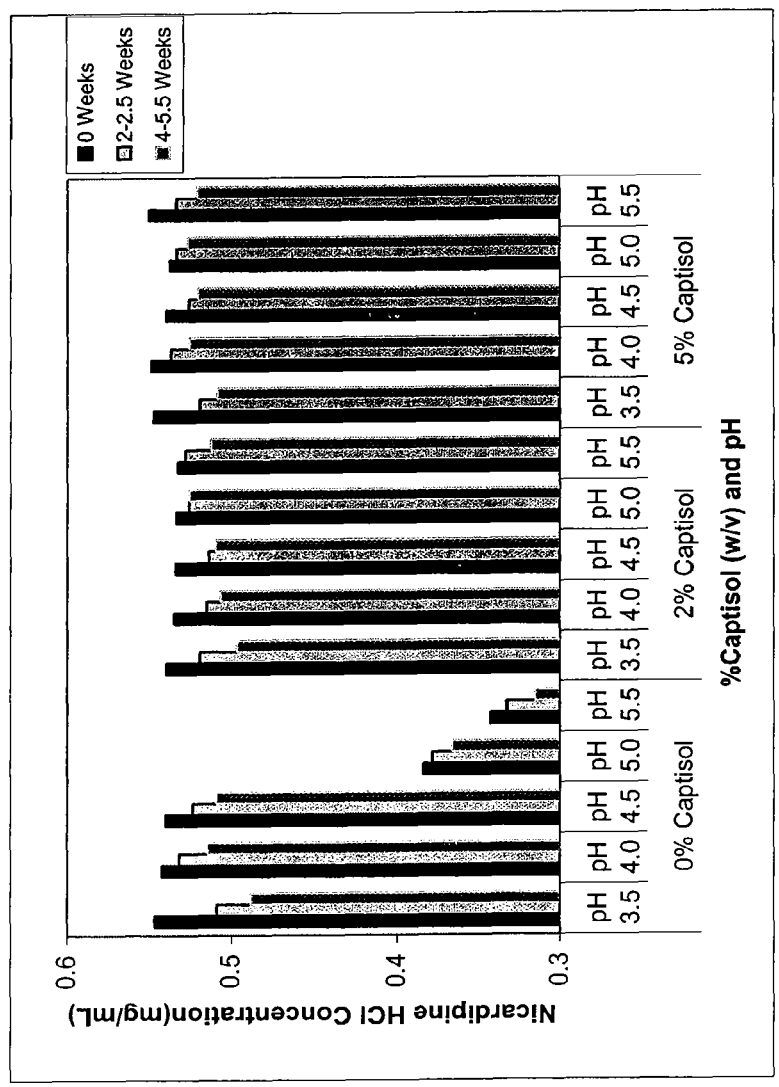
FIG. 2A: Stability study of nicardipine HCl formulations as a function of pH and CAPTISOL® concentration to evaluate nicardipine HCl concentration changes as a function of storage time at 55° C.
Figure 2B:
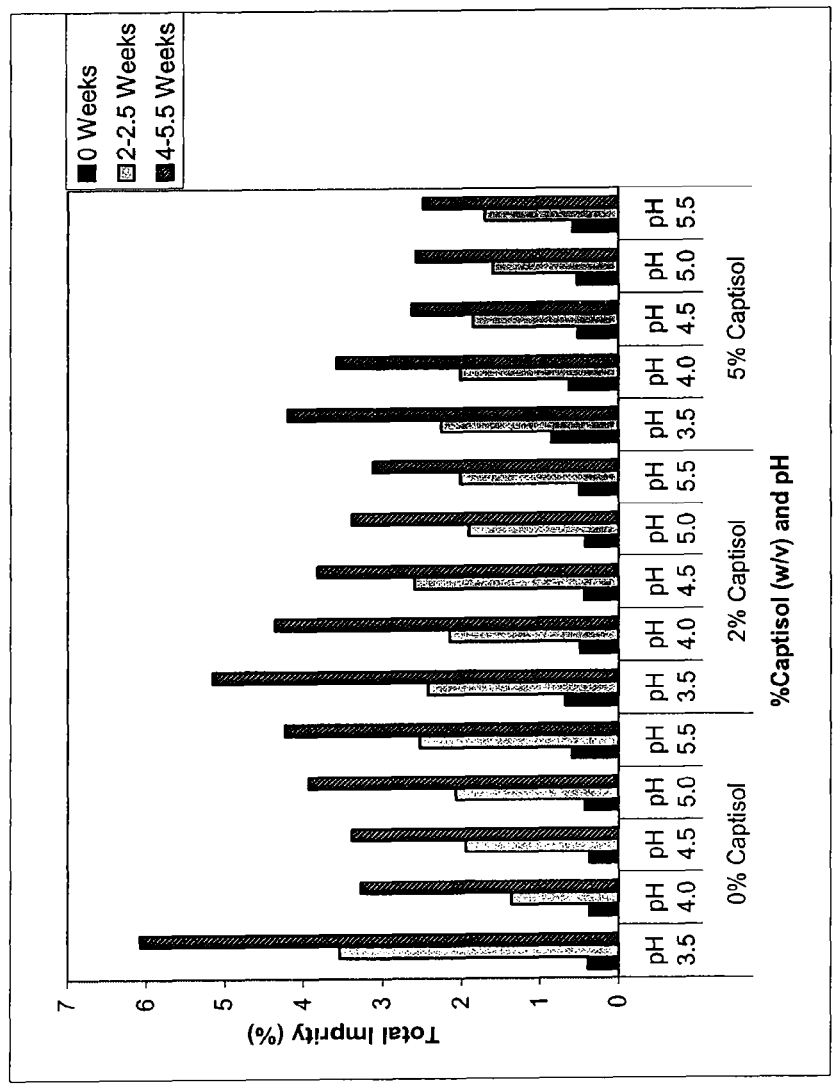
FIG. 2B: Stability study of nicardipine HCl formulations as a function of pH and CAPTISOL® concentration to evaluate % total impurity formation as a function of storage time at 55° C.

As shown in FIG. 2B, the Applicants have discovered that the use of CAPTISOL® (sulphobutylether β-cyclodextrin) enhances the solubility of nicardipine and reduces the total impurities formed upon storage of the compositions, particularly at the higher pHs. This discovery allows the development of higher concentration formulations comprising nicardipine at pH closer to the physiological pH range, and which can be used for direct intravenous administration without dilution.

Preparation of Pharmaceutical Compositions

The inclusion complex of the nicardipine and the sulfoalkylated β-cyclodextrin derivative may be prepared from aqueous solutions, slurries or pastes of nicardipine and the derivative(s) according to conventional methods. Solutions can be prepared by adding an aqueous solution of cyclodextrin to a buffered solution of the nicardipine salt with stirring until mixed In some embodiments, stable formulations useful in parenteral administration are made by: (a) dissolving an effective amount of nicardipine and/or a pharmaceutically acceptable salt thereof into a suitable liquid containing at least one buffering agent and at least one of a co-solvent and a complexing agent to form a pre-mixed solution, (b) adjusting the pH of the pre-mixed solution to a pH between 3.5 and 7.5, and (c) filling pharmaceutically acceptable containers with the pre-mixed solution.

In other embodiments, stable formulations useful in parenteral administration are made by: (a) dissolving an effective amount of nicardipine and/or a pharmaceutically acceptable salt thereof into a suitable liquid containing at least one buffering agent and at least one of a co-solvent to form a pre-mixed solution, (b) adjusting the pH of the pre-mixed solution to a pH between 3.5 and 7.5, and (c) filling pharmaceutically acceptable containers with the pre-mixed solution.

Procedures for filling pharmaceutical compositions in pharmaceutically acceptable containers, and their subsequent processing are known in the art. A sterile composition, as used herein, means a composition that been brought to a state of sterility and has not been subsequently exposed to microbiological contamination, i.e., the container holding the sterile composition has not been compromised. These procedures can be used to produce sterile pharmaceutical drug products often required for health care. See, e.g., Center for Drug Evaluation and Research (CDER) and Center for Veterinary Medicine (CVM), "Guidance for Industry for the Submission Documentation for Sterilization Process Validation in Applications for Human and Veterinary Drug Products", (November 1994). Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

In some embodiments, the compositions are terminally sterilized. Terminal sterilization can be used to destroy all viable microorganisms within the final, sealed container containing the pharmaceutical composition. Heat, radiation, and chemical means of sterilization are available. An autoclave is typically used to accomplish terminal heat-sterilization of drug products in their final packaging. Typical autoclave cycles in the pharmaceutical industry to achieve terminal sterilization of the final product are 121° C. for at least 10 minutes. Additional means of sterilization include gamma irradiation and ethylene oxide treatment.

Sterile pharmaceutical compositions may also be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the compositions can be sterile filled into a container to avoid the heat stress of terminal sterilization.

Preparation of Cyclodextrins

Suitable sulfoalkylated β-cyclodextrins for use in the compositions described herein include the sulfoalkyl ether β-cyclodextrin derivatives described in U.S. Pat. No. 5,376,645, which is incorporated by reference in its entirety, and particularly with reference to structures, properties, and manufacture of the sulfoalkylated β-cyclodextrin derivative disclosed therein. These derivatives are of the formula:

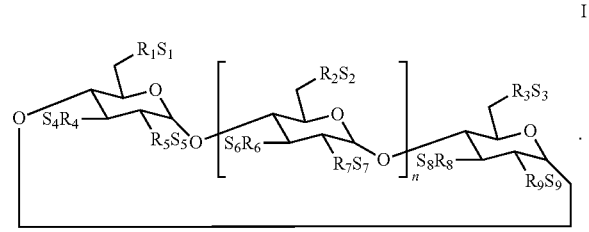

I

Wherein n is 4, 5 or 6; $R_1$, $R_2$, $R_3$, $R_4$, $R_5$, $R_6$, $R_7$, $R_8$ and $R_9$ are each independently, O$^-$ or a O—($C_{2-6}$ alkylene)SO$_3^-$ group, wherein at least one of $R_1$ and $R_2$ is independently a O—($C_{2-6}$ alkylene)-SO$_3^-$ group, preferably a O—(CH$_2$)$_m$ SO$_3^-$ group, wherein m is 2 to 6, or more, or 2 to 4, (e.g. OCH$_2$CH$_2$CH$_2$SO$_3^-$ or OCH$_2$CH$_2$CH$_2$CH$_2$SO$_3^-$); and $S_1$, $S_2$, $S_3$, $S_4$, $S_5$, $S_6$, $S_7$, $S_8$ and $S_9$ are each, independently, a pharmaceutically acceptable cation which includes, for example, H$^+$, alkali metals (e.g. Li$^+$, Na$^+$, K$^+$), alkaline earth metals (e.g., Ca$^{+2}$, Mg$^{+2}$), ammonium ions and amines cations such as the cations $C_{1-6}$ alkylamines, piperidine, pyrazine, $C_{1-6}$ alkanolamine and $C_{4-8}$ cycloalkanolamine.

In another preferred embodiment, $R_1$ is a O—($C_{2-6}$ alkylene)-SO$_3^-$ group, a O—(CH$_2$)$_m$SO$_3^-$ group, (e.g. OCH$_2$CH$_2$CH$_2$SO$_3^-$ or OCH$_2$CH$_2$CH$_2$CH$_2$SO$_3^-$); $R_2$ to $R_9$ are O$^-$; and $S_1$ to $S_9$ are as defined as above.

In another preferred embodiment, $R_1$, $R_2$ and $R_3$ are each, independently, a O—($C_{2-6}$-alkylene)-SO$_3^-$ group, preferably a O—(CH$_2$)$_m$SO$_3^-$ group, (e.g. OCH$_2$CH$_2$CH$_2$SO$_3^-$ or OCH$_2$CH$_2$CH$_2$CH$_2$SO$_3^-$); $R_4$ to $R_9$ are O$^-$; and $S_1$ to $S_9$ are as defined above.

In another preferred embodiment, $R_1$ to $R_3$ are as defined above and at least one of $R_4$, $R_6$ and $R_8$ is a O—$C_{2-6}$-alkylene-SO$_3^-$ group, preferably a O—(CH$_2$)$_m$SO$_3^-$ group (e.g. OCH$_2$CH$_2$CH$_2$SO$_3^-$ or OCH$_2$CH$_2$CH$_2$CH$_2$SO$_3^-$); $R_5$, $R_7$ and $R_9$ are O$^-$; and $S_1$ to $S_9$ are as defined as above.

In another embodiment, the derivatized β-cyclodextrin is the monosulfobutyl ether of β-cylcodextrin. In still yet another embodiment, the derivatized β-cyclodextrin is sulfobutylether β-cyclodextrin (CAPTISOL®). CAPTISOL® is a heterogeneous material containing multiple species of sulfobutylether β-cyclodextrin which differ in their degrees of sulfobutylation: an average of seven of the available 21 hydroxyls on the parent β-cyclodextrin are derivatized with sulfobutyl ether groups. The chemical name and CAS registry number for CAPTISOL® are β-cyclodextrin sulfobutyl ether, sodium salt [182410-00-0]. The chemical formula is $C_{42}H_{70-n}$.($C_4H_8SO_3Na$)$_n$.xH$_2$O, where n=approximately 6.5. Thus, CAPTISOL® contains some material with 2, 3, 4, 5, 6, 7, 8, 9, 10, and perhaps a very small amount of 1 and 11 degrees of substitution. CAPTISOL® generally is manufactured such that the average degree of substitution (DS) is about 7, and generally between 6.0 and 7.1. Accordingly, in some embodiments, the sulfobutylated β-cyclodextrin is one having an average of from 4 to 8, 6 to 8, 5 to 7, or 6 to 7.5 degrees of sulfobutylation. In other embodiments, the sulfobutylated β-cyclodextrin comprises species which have one or more of 4, 5, 6, 7, 8, or 9 degrees of sulfobutylation or any degree of sulfobutylation per the above formula. Accordingly, in some embodiments, the sulfobutylated β-cyclodextrin is one having an average of from 4 to 8, 6 to 8, 5 to 7, or 6 to 7.5 degrees of sulfobutylation.

In another embodiment, $R_1$, $R_2$, $R_3$, $R_4$, $R_6$ and $R_8$ are each, independently, a O—($C_{2-6}$-alkylene)-SO$_3^-$ group, a O—(CH$_2$)$_m$SO$_3^-$ group (e.g. OCH$_2$CH$_2$CH$_2$ SO$_3^-$ or OCH$_2$CH$_2$CH$_2$CH$_2$SO$_3^-$); $R_5$, $R_7$ and $R_9$ are O$^-$; and $S_1$ to $S_9$ are as defined above.

The terms "alkylene" and "alkyl" with regard to the formula for the sulfoalkyl ether cyclodextrin derivatives (e.g., in the O—($C_{2-6}$-alkylene)SO$_3^-$ group or in the alkylamines) include both linear and branched, saturated and unsaturated (i.e., containing one double bond) divalent alkylene groups and monovalent alkyl groups, respectively. The term "alkanol" with regard to the sulfoalkyl ether cyclodextrin derivatives likewise includes both linear and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl)cyclic alcohols.

With regard to compositions comprising nicardipine and a cyclodextrin derivative(s). In some embodiments, the derivatives have the structure set out in formula (1), where the composition overall contains on the average at least 1 and up to 3n+6 alkylsulfonic acid moieties per cyclodextrin molecule (n is 4, 5 or 6). The present invention also provides nicardipine compositions containing essentially only one single type of cyclodextrin derivative.

Suitable cyclodextrin derivatives are either substituted at least at one of the primary hydroxyl group (i.e., at least one of $R_1$ to $R_3$ is a substituent), or they are substituted at both the primary hydroxyl group and at the 3-position hydroxyl group (i.e., both at least one of $R_1$ to $R_3$ and at least one of $R_4$, $R_6$ and $R_8$ are a substituent).

Methods for making the sulfoalkyl ether cyclodextrin derivatives are well known in the art and are taught in U.S. Pat. No. 5,376,645. Methods for forming complexes of the derivatives with a drug are also well known in the art as disclosed in U.S. Pat. No. 5,376,645.

Alternative Aspects

In an alternative aspect, the present invention relates to pre-mixed, ready-to-use, injectable pharmaceutical compositions comprising a cardiac medication or a pharmaceutically acceptable salt thereof, and at least one of a co-solvent and a complexing agent, and a buffering agent. The composition may further comprise a tonicity agent. The compositions are preferably isotonic. The pH of the compositions is preferably between 3 and 7. The compositions are preferably packaged in a pharmaceutically acceptable container, such as an intravenous bag, syringe or vial. Preferably, the compositions are used for the treatment of cardiovascular and cerebrovascular conditions. The present invention also relates to methods for preparing such compositions. In this other aspect, the term "pre-mixed", as used herein, means a pharmaceutical composition that is already mixed from the point of manufacture and does not require dilution or further processing before administration. The term "pre-mixed" may also mean a pharmaceutical composition wherein the liquid solution and the active pharmaceutical ingredient are separated from the point of manufacture and in storage, such as when the solution is stored in an intravenous bag and the active pharmaceutical ingredient is lyophilized and stored in a vial that is connected to the bag, but not in fluid contact with the solution until just before administration to a patient. Preferably, the pharmaceutical compositions are aqueous solutions that are administered by injection. Alternatively, the pharmaceutical compositions may be lyophilized and then reconstituted in isotonic saline, for example, before intravenous administration.

In this alternative aspect, the pharmaceutical compositions of the present invention comprise a cardiac medication or a pharmaceutically acceptable salt thereof. Examples of classes of cardiac medications include beta-blockers, calcium channel antagonists, angiotensin converting enzyme inhibitors, diuretics, vasodilators, nitrates, anti-platelet medications and anti-coagulants. Preferably, the cardiac medication is a calcium channel antagonist or a pharmaceutically acceptable salt thereof. More preferably, the cardiac medication is a dihydropyridine derivative or a pharmaceutically acceptable salt thereof. Most preferably, the cardiac medication is nicardipine or a pharmaceutically acceptable salt thereof. Examples of pharmaceutically acceptable salts of nicardipine are hydrochlorides, sulfates, phosphates, acetates, fumarates, maleates and tartarates. The preferred pharmaceutically acceptable salt of nicardipine is nicardipine hydrochloride. The pharmaceutical compositions may comprise 0.05-1.5 mg/ml of nicardipine or a pharmaceutically acceptable salt thereof. Preferably, the pharmaceutical compositions comprise 0.15-0.35 mg/ml of nicardipine or a pharmaceutically acceptable salt thereof. More preferably, the compositions comprise 0.2-0.3 mg/ml of nicardipine or pharmaceutically acceptable salt thereof. Nicardipine and its pharmaceutically acceptable salts, their preparation, and their use are known in the art. For example, they are disclosed in, among other references, U.S. Pat. No. 3,985,758, which is incorporated herein by reference in its entirety.

In some embodiments, the pharmaceutical compositions comprise 0.1-15 mg/ml nicardipine or a pharmaceutically acceptable salt thereof. For example, suitable concentrations of nicardipine or a pharmaceutically acceptable salt thereof, include, but are not limited to: 0.1-15 mg/ml, 0.1-10 mg/ml, 0.1-5 mg/ml, 0.1-3.0 mg/ml, 0.1-2.0 mg/ml, 0.1-1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml or 0.1 mg/ml.

In this alternative aspect, the pharmaceutical compositions can be used to treat cardiac conditions. Preferably, the compositions can be used to treat conditions that are alleviated by the administration of calcium channel antagonists, such as cardiovascular and cerebrovascular conditions. Cardiovascular conditions that can be treated with the pharmaceutical compositions of the present invention include angina, ischemic, systemic arterial hypertension, congestive heart failure, coronary artery disease, myocardial infarction, cardiac arrhythmias, cardiomyopathies and arteriosclerosis. Cerebrovascular conditions that can be treated with the pharmaceutical compositions of the present invention include pulmonary hypertension, cerebral insufficiency and migraine. Preferably, the compositions are used to treat hypertension.

In this alternative aspect, the pharmaceutical compositions of the present invention also comprise at least one of a cosolvent and a complexing agent. Therefore, the compositions may comprise a cosolvent, a complexing agent, multiple cosolvents, multiple complexing agents, a cosolvent and a complexing agent, a cosolvent and multiple complexing agents, a complexing agent and multiple cosolvents, or multiple cosolvents and multiple complexing agents.

In this alternative aspect, Nicardipine and its pharmaceutically acceptable salts are only slightly soluble in water. Cosolvents and complexing agents help solubilize nicardipine in the aqueous solution of the pharmaceutical composition. Cosolvents and complexing agents are especially beneficial when a high concentration of nicardipine is present, such as in the compositions of the present invention. An advantage of the compositions of the present invention is that they have a high concentration of nicardipine, which allows the composition to be administered using a lower volume of intravenous fluid. Such compositions can be a treatment option for a greater number of patients, especially volume restricted patients.

In this alternative aspect, patients and medical conditions that may benefit from a higher concentration and lower fluid volume of nicardipine include, but are not limited to, the following: acute congestive cardiac failure; pediatrics; hypertensive crises in elderly patients where fluid overload is a major concern; all acute stroke areas including AIS, ICH and SAH to control blood pressure; controlled hypotension during surgical procedures including cardiothoracic surgery (CABG, coarctation of the aorta, etc.), spinal surgeries, and head and neck surgeries; and neurosurgery for the control of breakthrough hypertension post carotid endarterectomy, traumatic brain injury and potential treatment of hypertension and vasospasm.

In this alternative aspect, in addition to enhancing solubility, cosolvents and complexing agents enhance the stability of the pharmaceutical compositions. Furthermore, changes may be made to the concentration of cosolvents and complexing agents in the pharmaceutical compositions in order to adjust the tonicity of the pharmaceutical compositions. Pharmaceutically acceptable cosolvents are known in the art and are commercially available. Typical cosolvents include polyethylene glycol (PEG), propylene glycol (PG), ethanol and sorbitol. Preferably, the cosolvent concentration is 0.1-10% weight/volume percent, which will depend on the pH of the composition. More preferably, the cosolvent concentration is 0.1-5%. Most preferably, the cosolvent concentration is 0.1-2%. Preferred cosolvents for the pharmaceutical compositions are propylene glycol and sorbitol. Preferably, the concentration of propylene glycol is 0.1-2%. More preferably, the concentration of propylene glycol is 0.1-1%. Most preferably, the concentration of propylene glycol is 0.3%. A preferred concentration of sorbitol is 0.1-2%. An even more preferred concentration of sorbitol is 0.1-1%. A most preferred concentration of sorbitol is 0.5%.

In this alternative aspect, pharmaceutically acceptable complexing agents are known in the art and commercially available. Typical complexing agents include cyclodextrins, such as natural cyclodextrins and chemically modified cyclodextrins. Preferably, the complexing agent is a beta cyclodextrin. Preferred complexing agents for the pharmaceutical compositions are 2-hydroxypropyl-β-cyclodextrin (2HPBCD) and sulfobutylether-β-cyclodextrin (SBEBCD). Preferably, the complexing agent concentration is 0.1-25% weight/volume percent. More preferably, the complexing agent concentration is 0.1-10%. Most preferably, the complexing agent concentration is 0.1-5%. Preferably, the concentration of 2HPBCD is 15-25%. More preferably, the concentration of 2HPBCD is 20-25%. The preferred concentration of SBEBCD is 0.1-10%. An even more preferred concentration of SBEBCD is 0.1-5%. The most preferred concentration of SBEBCD is 0.75 to 1%.

In addition, the pharmaceutical compositions in this alternative aspect can comprise a buffering agent. However, the compositions may comprise multiple buffering agents. The pharmaceutical compositions of the present invention are preferably close to physiological pH in order to minimize the incidence of phlebitis upon administration. However, the pH of the pharmaceutical composition also affects the solubility and stability of nicardipine in the composition. Generally, as the pH of the pharmaceutical composition increases, the aqueous solubility of nicardipine decreases. As a result, it is difficult to solubilize nicardipine close to physiological pH. In addition, the composition should have sufficient buffering capacity such that the solution does not precipitate upon dilution with blood when administered.

Buffering agents are used to adjust the pH of the pharmaceutical compositions in this alternative aspect as well. The pH of the compositions is preferably between 3.5 and 7.5. More preferably, the pH of the compositions is between 4 and 6. Even more preferably, the pH of the compositions is between 4.0 and 5.5. Most preferably, the pH of the composition is between 4.5 and 5.2.

In this alternative aspect, typical buffering agents include acetate, glutamate, citrate, tartrate, benzoate, lactate, histidine or other amino acids, gluconate, phosphate and succinate. The preferred buffering agents are acetate and succinate. A preferred buffering agent concentration is 1-100 mM. A more preferred buffering agent concentration is 1-50 mM. An even more preferred buffering agent concentration is 25-35 mM.

In this alternative aspect, preferably, the pharmaceutical compositions of the present invention are isotonic, i.e., in the range of 270-328 mOsm/kg. However, the compositions may have a tonicity in the range of 250-350 mOsm/kg. Therefore, the compositions may be either slightly hypotonic, 250-269 mOsm/kg, or slightly hypertonic, 329-350 mOsm/kg. Preferably, the tonicity of the pharmaceutical compositions is rendered isotonic by adjusting the concentration of any one or more of cosolvent, complexing agent and buffering agent in the solution.

In this alternative aspect, the pharmaceutical compositions of the present invention may further comprise a tonicity agent. However, the compositions may further comprise multiple tonicity agents. Tonicity agents are well known in the art and commercially available. Typical tonicity agents include sodium chloride and dextrose. The preferred tonicity agent is sodium chloride. A preferred tonicity agent concentration is 1-200 mM. A more preferred tonicity agent concentration is 75-125 mM. An even more preferred tonicity agent concentration is 90-110 mM.

The pharmaceutical compositions of the present invention are preferably packaged in pharmaceutically acceptable containers in this alternative aspect. Pharmaceutically acceptable containers include intravenous bags, bottles, vials, and syringes. Preferred containers include intravenous bags and syringes, which are preferably polymer-based, and vials and intravenous bottles, which are preferably made of glass. It is also preferred that the components of the container that come into contact with the pharmaceutical composition do not contain polyvinylchloride (PVC). The most preferred container is an intravenous bag that does not have any PVC containing components in contact with the pharmaceutical composition. It is also desirable to protect the pharmaceutical compositions from light. Therefore, the container may, optionally, further comprise a light barrier. A preferred light barrier is an aluminum overpouch.

This alternative aspect also provides methods as described above for preparing the pharmaceutical compositions which are sterile.

EXAMPLES

The following Examples are intended to be illustrative and not limiting as to the general disclosure. Examples 6 through 11 disclose specific embodiments of the pharmaceutical compositions that are principally illustrative of the alternative aspects described herein.

Example 1

Phase-solubility Study to Evaluate Complexation of Nicardipine HCl and CAPTISOL® (Sulphobutylether β-cyclodextrin) as a Function of pH in this phase-solubility study, nicardipine HCl, in amounts that exceeded its solubility, was taken into vials containing buffers in the pH range of 3.6-7.4 and containing CAPTISOL® in the concentration range of 2-40% w/v. These evaluations were also done for buffer solutions containing no CAPTISOL®. The vials were sealed and shaken at room temperature until equilibrium was reached. Subsequently, test sample aliquots were withdrawn, filtered, and drug concentration was determined by RP-HPLC with UV detection.

As shown in FIG. 1, the solubility of nicardipine HCl decreased with increased pH. At a given pH value, as CAPTISOL® concentration is increased the solubility of nicardipine HCl is increased. Because of this significant increase in solubility, use of CAPTISOL® allows solubilization of the drug closer to physiological pH's.

Example 2

Stability Evaluation of Nicardipine HCl Formulations

Nicardipine HCl at a target concentration of 0.5 mg/ml in 10 mM Na-acetate buffer was studied. All the formulations were filled in amber glass vials with coated elastomeric closures (e.g. Daikyo Flurotech Stoppers) nad terminally sterilized. The pH values evaluated include 3.5, 4.0, 4.5, 5.0 and 5.5. Formulations either contained no CAPTISOL® (sulphobutylether β-cyclodextrin), or contained 2 or 5% CAPTISOL®. Vials were inverted and stored at 55° C. for up to approximately 5 weeks. At each stability time point, test sample aliquots were withdrawn, and the nicardipine concentration and impurity levels were determined by RP-HPLC with UV detection.

Stability evaluations were done by monitoring (1) the loss in nicardipine HCl concentration (potency) (see, FIG. 2A) and (2) formation of total product-related impurities as a function of time (FIG. 2B). Testing done under these stressed conditions helps accelerate product degradation and project product viability at relevant storage conditions in a shorter period of time.

Based on published literature, activation energies for drug decompositions usually fall in the range of 12 to 24 Kcal/mol, with typical value of 19-20 Kcal/mol. Under these conditions (assumption Ea=19.4 Kcal/mol) ~2.9 weeks storage at 55° C. corresponds to a product with 18 months expiration at 25° C. (see, e.g., Connors, K. A., et al., Chemical Stability of Pharmaceuticals, A Handbook for Pharmacists, John Wiley & Sons, 2d ed. 1986).

As shown in FIG. 2A, for CAPTISOL formulations, loss in product potency (i.e. drug concentration) is reduced over the pH range of 3.5-5.5. For example, for formulations without CAPTISOL®, the target concentration of 0.5 mg/mL could not be attained for formulations at pH 5.0 and 5.5. However, for formulations with 2 and 5% CAPTISOL®, drug loss was less than 5% for all formulations in the pH range of 4.0-5.5.

The formation of all product-related impurities is shown in FIG. 2B. It was observed that impurity levels were highest for the pH 3.5 formulations without CAPTISOL®. At this pH, as the CAPTISOL® concentration was increased, the impurity levels were reduced. It was also observed that the effect of pH on impurity formation was different for the CAPTISOL® and the non-CAPTISOL® formulations. For the non-CAPTISOL® formulations, % impurity levels increased with pH, however, for all CAPTISOL® formulations, the reverse trend was observed (see, FIG. 2B). Reduction in the total impurity levels was observed as the CAPTISOL® concentration was increased in the formulations. For example, total impurity levels were the lowest for formulations containing 5% CAPTISOL®.

Based on these stability results, for both CAPTISOL® and non-CAPTISOL® formulations, a pH range that allows development of drug product with acceptable stability at room temperature can be identified. For non-CAPTISOL® formulations, the pH range is limited to 3.5<pH<5.0. CAPTISOL® formulations allow for a wider pH range for product development, 3.5<pH≤5.5, enabling the development of a formulation closer to physiological. In addition, at pH>3.5, the CAPTISOL® formulations were also associated with reduced adsorptive drug loss and total impurity formation upon storage in pharmaceutically acceptable container systems.

Example 3

Effect of CAPTISOL® (Sulphobutylether β-cyclodextrin) Formulations on Nicardipine Hydrochloride Precipitation in the Static Precipitation Model In this study, 0.3 mg/mL nicardipine HCl formulations made in 30 mM Na-acetate buffer, pH 4.5, containing 0-3% w/v CAPTISOL® were evaluated for their potential for precipitation at the site of injection. Various dilutions of each formulation were prepared using a solution at pH 7.4 with buffering capacity comparable to blood (e.g., pH 7.4 Sorensen's phosphate buffer), and sample opacity was measured by monitoring the % Transmission of light at a wavelength of 490 nm using a spectrophotometer. For improved assay precision, this method was developed using a 96-well plate format. A dilution ratio of 1.0 would correspond to a test sample with no dilution by the pH 7.4 buffer, a dilution ratio of 0.5 would correspond to a test sample where the formulation is volumetrically diluted 1:1 with the pH 7.4 buffer, and likewise, a dilution ratio of zero would correspond to a test sample containing only the pH 7.4 buffer.

Figure 3:
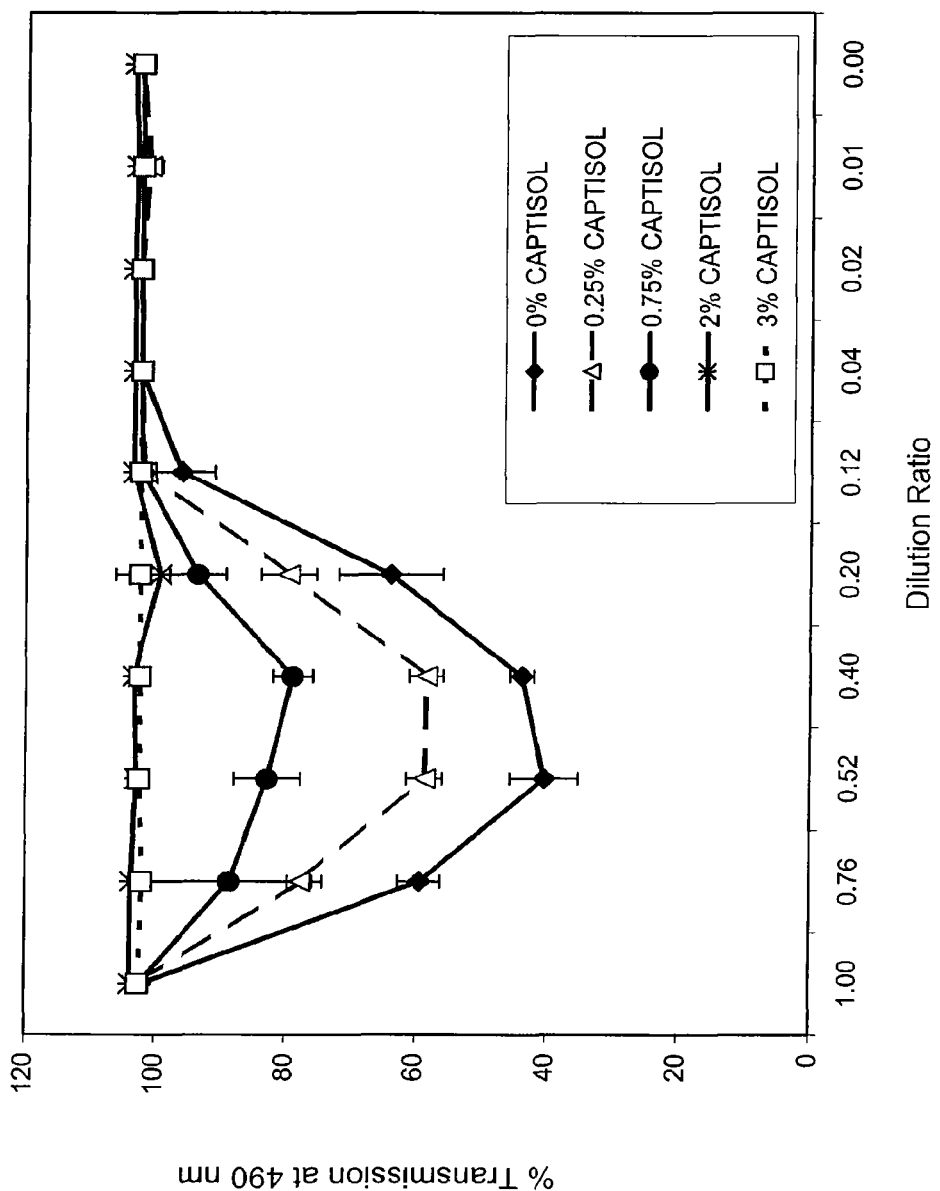
FIG. 3. Evaluation of precipitation potential as a function of the dilution factor for the evaluated CAPTISOL® formulations in an in vitro static precipitation model.

FIG. 3 shows transmission as a function of the dilution factor for the evaluated CAPTISOL® formulations. A decrease in the measured % Transmission value is indicative of increased opacity due to drug precipitation. Study results clearly support that as the concentration of CAPTISOL® is increased in the formulation, sample opacity, which is indicative of the potential for drug precipitation upon dilution with blood at the site of injection, is considerably reduced. Preliminary results (see Example 5) with a dynamic model (the complex is injected into a flowing solution maintained at the flow rate of blood) support the ability of CAPTISOL® to reduce precipitation as well.

Example 4

Figure 4:
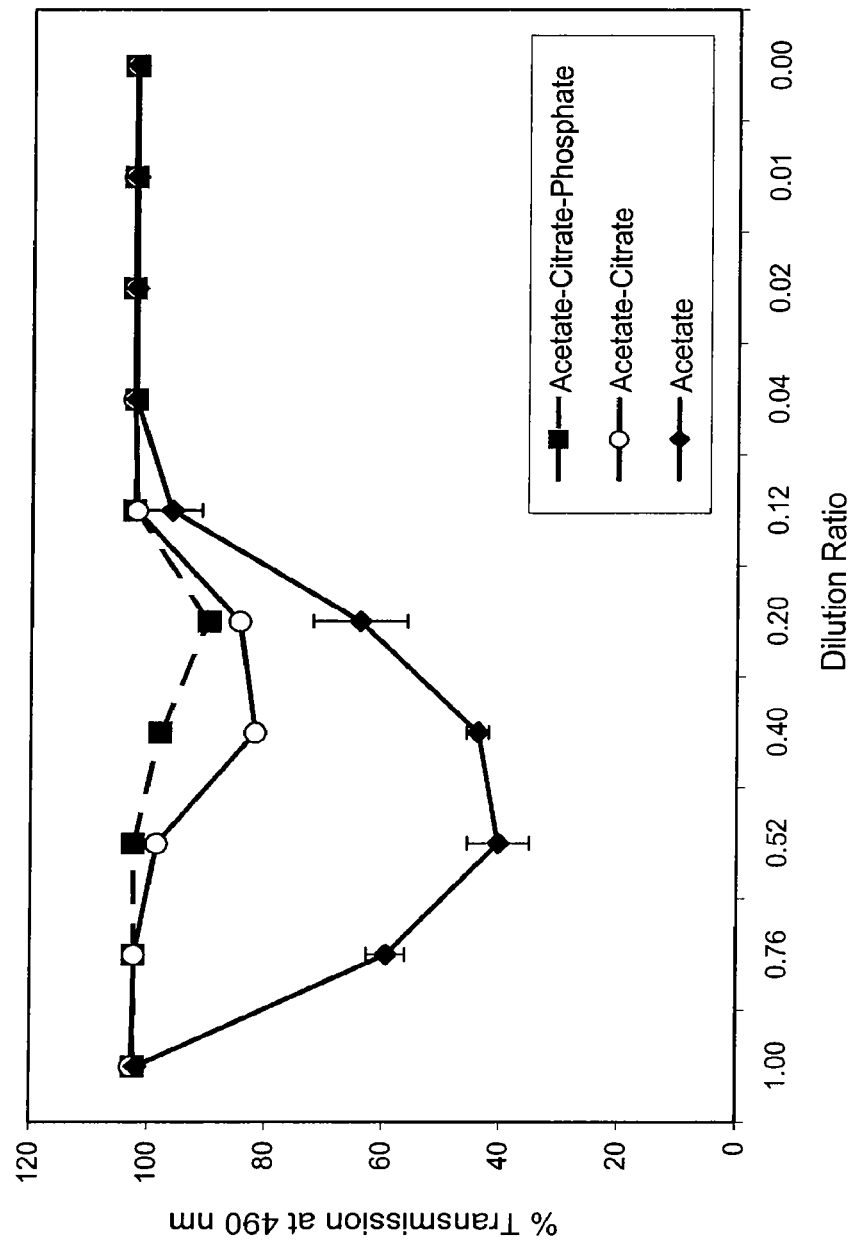
FIG. 4. Evaluation of precipitation potential as a function of the dilution factor for the evaluated mixed buffer formulations in an in vitro static precipitation model.

Effect of Mixed-Buffer Formulations on Nicardipine Hydrochloride Precipitation in the Static Precipitation Model FIG. 4 shows the measured opacity as a function of the dilution factor for the evaluated mixed buffer formulations with the same procedure as Example 3. The formulations were as follows:

Acetate-Citrate-Phosphate Formulation: 0.3 mg/ml Nicardipine HCl, 30 mM Acetate, 30 mM Citrate, 30 mM Phosphate, 69.5 mM NaCl, pH 4.5, Acetate-Citrate Formulation: 0.3 mg/ml Nicardipine HCl, 30 mM Acetate, 30 mM Citrate, 97 mM NaCl, pH 4.5, Acetate Formulation: 0.3 mg/mL Nicardipine HCl, 30 mM Acetate, pH 4.5.

As observed for the CAPTISOL® (sulphobutylether β-cyclodextrin) formulations, the decrease in opacity clearly support that the use of combination of buffers with varying pKa such that sufficient buffering capacity is obtained in the pH range of 3.5-7.5 is also an effective strategy to minimize potential for drug precipitation at the site of injection.

Example 5

Figure 5:
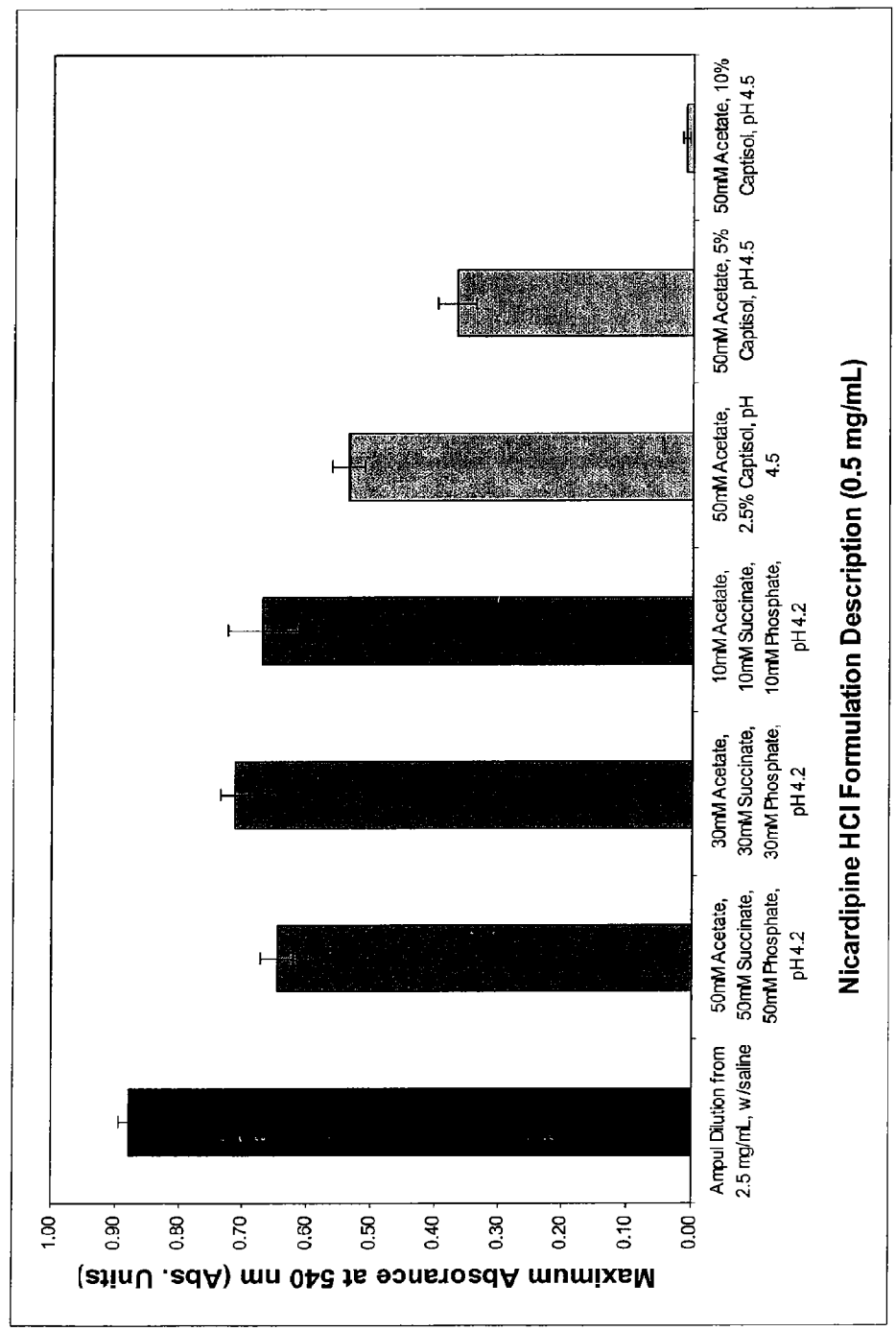
FIG. 5. Evaluation of precipitation potential of CAPTISOL® and mixed buffer formulations in an in vitro dynamic precipitation model.

Study to Evaluate Potential for Nicardipine Precipitation at Site of Injection Using a Dynamic In Vitro Precipitation Model FIG. 5 shows the experiment results to predict the potential for drug precipitation using a dynamic in-vitro testing procedure (Reference: Yalkowsky et. al, Journal of Pharmaceutical Sciences, Volume 92, No. 8, 2003). The model simulates the injection of formulations into vein and detects precipitation. All formulations in FIG. 5 contained 0.5 mg/ml Nicardipine HCl. The formulations from left to right in FIG. 5 were as follows:

0.5 mg/mL Nicardipine HCl diluted rfom the current 2.5 mg/mL ampul product using saline.

0.5 mg/mL Nicardipine HCl, 50 mM Acetate, 50 mM Succinate and 50 mM Phosphate buffer, 106 mM NaCl, pH 4.2.

0.5 mg/ml Nicardipine HCl, 138 mM NaCl in 30 mM Acetate, 30 mM Succinate and 30 mM Phosphate buffer, pH 4.2.

0.5 mg/mL Nicardipine HCl, 152 mM NaCl in 10 mM Acetate, 10 mM Succinate and 10 mM Phosphate buffer, pH 4.2.

0.5 mg/mL Nicardipine HCl, 130 mM NaCl and 2.5% (w/v) CAPTISOL® (sulphobutylether β-cyclodextrin) in 50 mM Acetate buffer, pH 4.5.

0.5 mg/mL Nicardipine HCl, 90 mM NaCl and 5.0% (w/v) CAPTISOL® in 50 mM Acetate buffer, pH 4.5.

0.5 mg/mL Nicardipine HCl, 20 mM NaCl and 10.0% (w/v) CAPTISOL® in 50 mM Acetate buffer, pH 4.5.

Each of above formulation was injected at a 5 ml/min injection rate (triplicate), into a flowing isotonic Sorensen's Phosphate buffer solution with buffering capacity comparable to blood (pH 7.4, with a flow rate at 5 ml/min). The mixture of various formulations and Sorenson's buffer passed through a flow-cell of a UV detector and the resulting precipitate was measured by monitoring the absorbance at 540 nm. A decreased maximum absorbance indicates a decreased potential for precipitation. Consistent with results demonstrated in the static model (FIGS. 3 and 4), the results in FIG. 5 from the dynamic in vitro precipitation model indicate that CAPTISOL® is effective in minimizing drug precipitation. For example, the precipitation level decreased when the concentrations of CAPTISOL® increased from 2.5% to 10.0% (w/v). In addition, the use of mixed buffer formulations, also reduced the potential for drug precipitation.

Examples 6 through 11

Examples 6-11 illustrate experiments performed using specific embodiments. The experiments in Examples 6-11 were performed at 45° C. in order to simulate stressed conditions that cause sufficient product degradation in a relatively short period of time. Stability comparisons were done against the control formulation (CF) and/or the commercial product formulation (CPF) in order to assess relative differences in their degradation profiles. The CPF is a marketed drug product and, therefore, degradation behavior of the molecule is well understood as a function of temperature and time. Stability data are available for the marketed product up to 36 months at room temperature, 22-27° C., and 40° C.

The rationale used in this preliminary screening evaluation is that if the degradation kinetics of the evaluated formulation prototypes were comparable to the CPF at stressed temperatures, drug product stability would likely be comparable or better at room temperature. The current prototype formulation is stable for at least 18 months at 25° C., and therefore it is projected that the evaluated formulation prototypes can have comparable or better stability.

Example 6

Formulation Preparation and Analysis

Appropriate buffers, such as acetate or succinate, containing the desired cosolvents, such as sorbitol or propylene glycol, and/or complexing agents, such as SBEBCD or 2HPBCD, were prepared. Appropriate tonicity agents, such as sodium chloride, were prepared and added to some of the pharmaceutical compositions. Based upon the final formulation volume and the target drug concentration, usually 0.2-0.3 mg/mL, nicardipine was weighed into an appropriate glass container and prepared buffer was added to dissolve the drug. Tonicity agent, if any, was then added. The solution was then sonicated for up to 45 minutes to facilitate drug dissolution. Following drug dissolution, the solution was filtered through a 0.45 μm syringe filter (Acrodisc LC 13 mm Syringe filter, PVDF Membrane from Life Sciences, PN 4452T). When filtering, the first few drops were discarded and the remaining solution was collected into another glass container. The prepared formulations were subsequently dispensed into either vials or intravenous bags.

The following isotonic pharmaceutical compositions were made according to the above protocol:

Pharmaceutical Composition 1 (PC 1): 0.2-0.3 mg/ml nicardipine hydrochloride, 3.7% sorbitol, and 50 mM Na-acetate, wherein the pH of the composition is 5.0.

Pharmaceutical Composition 2 (PC 2): 0.2-0.3 mg/ml nicardipine hydrochloride, 1.7% propylene glycol, and 50 mM Na-acetate, wherein the pH of the composition is 5.0.

Pharmaceutical Composition 3 (PC 3): 0.2-0.3 mg/ml nicardipine hydrochloride, 2.8% sorbitol, and 50 mM Na-succinate, wherein the pH of the composition is 5.5.

Pharmaceutical Composition 4 (PC 4): 0.2-0.3 mg/ml nicardipine hydrochloride, 1.1% propylene glycol, and 50 mM Na-succinate, wherein the pH of the composition is 5.5.

Pharmaceutical Composition 5 (PC 5): 0.2-0.3 mg/ml nicardipine hydrochloride, 4.1% sorbitol, and 50 mM Na-acetate, wherein the pH of the composition is 3.5.

Pharmaceutical Composition 6 (PC 6): 0.2-0.3 mg/ml nicardipine hydrochloride, 1.9% propylene glycol, and 50 mM Na-acetate, wherein the pH of the composition is 3.5.

Pharmaceutical Composition 7 (PC 7): 0.2-0.3 mg/ml nicardipine hydrochloride, 4.1% sorbitol, and 50 mM Na-acetate, wherein the pH of the composition is 4.5.

Pharmaceutical Composition 8 (PC 8): 0.2-0.3 mg/ml nicardipine hydrochloride, 1.8% propylene glycol, and 50 mM Na-acetate, wherein the pH of the composition is 4.5.

Pharmaceutical Composition 9 (PC 9): 0.2-0.3 mg/ml nicardipine hydrochloride, 6.5% sulfobutylether-β-cyclodextrin, and 50 mM Na-succinate, wherein the pH of the composition is 5.5.

Pharmaceutical Composition 10 (PC 10): 0.2-0.3 mg/ml nicardipine hydrochloride, 6.5% sulfobutylether-β-cyclodextrin, and 50 mM Na-succinate, wherein the pH of the composition is 6.0.

Pharmaceutical Composition 11 (PC 11): 0.2-0.3 mg/ml nicardipine hydrochloride, 8.5% sulfobutylether-β-cyclodextrin, and 50 mM Na-succinate, wherein the pH of the composition is 5.5.

Pharmaceutical Composition 12 (PC 12): 0.2-0.3 mg/ml nicardipine hydrochloride, 8.5% sulfobutylether-β-cyclodextrin, and 50 mM Na-succinate, wherein the pH of the composition is 6.0.

Pharmaceutical Composition 13 (PC 13): 0.2-0.3 mg/ml nicardipine hydrochloride, 8.5% sulfobutylether-β-cyclodextrin, and 50 mM Na-acetate, wherein the pH of the composition is 5.0.

Pharmaceutical Composition 14 (PC 14): 0.2-0.3 mg/ml nicardipine hydrochloride, 8.5% sulfobutylether-β-cyclodextrin, and 50 mM Na-citrate, wherein the pH of the composition is 5.5.

Pharmaceutical Composition 15 (PC 15): 0.2-0.3 mg/ml nicardipine hydrochloride, 22.5% 2-hydroxypropyl-β-cyclodextrin, and 50 mM Na-acetate, wherein the pH of the composition is 5.0.

Pharmaceutical Composition 16 (PC 16): 0.2-0.3 mg/ml nicardipine hydrochloride, 22.5% 2-hydroxypropyl-β-cyclodextrin, and 50 mM Na-succinate, wherein the pH of the composition is 5.5.

Pharmaceutical Composition 17 (PC 17): 0.2-0.3 mg/ml nicardipine hydrochloride, 17.5% 2-hydroxypropyl-β-cyclodextrin, and 50 mM Na-acetate, wherein the pH of the composition is 5.0.

Pharmaceutical Composition 18 (PC 18): 0.2-0.3 mg/ml nicardipine hydrochloride, 17.5% 2-hydroxypropyl-β-cyclodextrin, and 50 mM Na-succinate, wherein the pH of the composition is 5.5.

Commercial Product (Ampul) Formulation (CPF): 2.5 mg/ml nicardipine hydrochloride, 2.5 mM citrate, and 5% sorbitol, wherein the pH of the composition is 3.5.

Control Formulation (CF): 0.3 mg/ml nicardipine hydrochloride, 2.5 mM citrate, and 5% sorbitol, wherein the pH of the composition is 3.5.

Pharmaceutical Composition 19 (PC 19): 0.3 mg/ml nicardipine hydrochloride, 50 mM sodium acetate, 50 mM sodium citrate, and 50 mM disodium succinate, wherein the pH of the composition is 3.5.

Pharmaceutical Composition 20 (PC 20): 0.3 mg/ml nicardipine hydrochloride, 50 mM sodium acetate, 50 mM sodium citrate, and 50 mM disodium succinate, wherein the pH of the composition is 4.5.

Pharmaceutical Composition 21 (PC 21): 0.3 mg/ml nicardipine hydrochloride, 50 mM sodium acetate, 50 mM sodium citrate, and 50 mM disodium succinate, wherein the pH of the composition is 5.0.

Pharmaceutical Composition 22 (PC 22): 0.3 mg/ml nicardipine hydrochloride, 50 mM sodium acetate, 50 mM sodium citrate, and 25 mM disodium succinate, wherein the pH of the composition is 5.5.

Pharmaceutical Composition 23 (PC 23): 0.3 mg/ml nicardipine hydrochloride, 4.1% sorbitol, and 50 mM sodium acetate, wherein the pH of the composition is 3.5.

Pharmaceutical Composition 24 (PC 24): 0.3 mg/ml nicardipine hydrochloride, 4.1% sorbitol, and 50 mM sodium acetate, wherein the pH of the composition is 4.5.

Pharmaceutical Composition 25 (PC 25): 0.3 mg/ml nicardipine hydrochloride, 3.7% sorbitol, and 50 mM sodium acetate, wherein the pH of the composition is 5.0.

Pharmaceutical Composition 26 (PC 26): 0.3 mg/ml nicardipine hydrochloride, 2.8% sorbitol, and 50 mM sodium acetate, wherein the pH of the composition is 5.5.

Pharmaceutical Composition 27 (PC 27): 0.3 mg/ml nicardipine hydrochloride, 1.9% propylene glycol, and 50 mM sodium acetate, wherein the pH of the composition is 3.5.

Pharmaceutical Composition 28 (PC 28): 0.3 mg/ml nicardipine hydrochloride, 1.8% propylene glycol, and 50 mM sodium acetate, wherein the pH of the composition is 4.5.

Pharmaceutical Composition 29 (PC 29): 0.3 mg/ml nicardipine hydrochloride, 1.7% propylene glycol, and 50 mM sodium acetate, wherein the pH of the composition is 5.0.

Pharmaceutical Composition 30 (PC 30): 0.3 mg/ml nicardipine hydrochloride, 1.1% propylene glycol, and 50 mM sodium succinate, wherein the pH of the composition is 5.5.

Pharmaceutical Composition 31 (PC 31): 0.3 mg/ml nicardipine hydrochloride, 6.5% sulfobutylether-β-cyclodextrin, and 50 mM sodium succinate, wherein the pH of the composition is 5.5.

Pharmaceutical Composition 32 (PC 32): 0.3 mg/ml nicardipine hydrochloride, 6.5% sulfobutylether-β-cyclodextrin, and 50 mM sodium succinate, wherein the pH of the composition is 6.0.

Pharmaceutical Composition 33 (PC 33): 0.3 mg/ml nicardipine hydrochloride, 22.5% 2-hydroxypropyl-β-cyclodextrin, and 50 mM sodium acetate, wherein the pH of the composition is 5.0.

Pharmaceutical Composition 34 (PC 34): 0.3 mg/ml nicardipine hydrochloride, 17% 2-hydroxypropyl-β-cyclodextrin, and 50 mM disodium succinate, wherein the pH of the composition is 5.5.

Pharmaceutical Composition 35 (PC 35): 0.3 mg/ml nicardipine hydrochloride, 0.3% propylene glycol, 0.5% sorbitol, 30 mM sodium acetate, and 90 mM NaCl, wherein the pH of the composition is 5.2.

Pharmaceutical Composition 36 (PC 36): 0.3 mg/ml nicardipine hydrochloride, 0.3% propylene glycol, 2.0% sorbitol, 30 mM sodium acetate, 45 mM NaCl, wherein the pH of the composition is 5.2.

Pharmaceutical Composition 37 (PC 37): 1.5 mg/ml nicardipine hydrochloride, 9% sulfobutylether-β-cyclodextrin, and 30 mM sodium acetate, wherein the pH of the composition is 4.5.

Pharmaceutical Composition 38 (PC 38): 1.5 mg/ml nicardipine hydrochloride, 9% sulfobutylether-β-cyclodextrin, and 30 mM sodium acetate, wherein the pH of the composition is 5.0.

Pharmaceutical Composition 39 (PC 39): 0.3 mg/ml nicardipine hydrochloride, and 30 mM sodium acetate, wherein the pH of the composition is 3.5.

Pharmaceutical Composition 40 (PC 40): 0.3 mg/ml nicardipine hydrochloride, and 30 mM sodium acetate, wherein the pH of the composition is 4.0.

Pharmaceutical Composition 41 (PC 41): 0.3 mg/ml nicardipine hydrochloride, and 30 mM sodium acetate, wherein the pH of the composition is 4.5.

Pharmaceutical Composition 42 (PC 42): 0.3 mg/ml nicardipine hydrochloride, 1.8% sulfobutylether-β-cyclodextrin, 30 mM sodium acetate, and 110 mM NaCl, wherein the pH of the composition is 5.0.

Pharmaceutical Composition 43 (PC 43): 0.3 mg/ml nicardipine hydrochloride, 1.8% sulfobutylether-β-cyclodextrin, 0.3% propylene glycol, 30 mM sodium acetate, and 85 mM NaCl, wherein the pH of the composition is 5.0.

Pharmaceutical Composition 44 (PC 44): 0.3 mg/ml nicardipine hydrochloride, 1.8% sulfobutylether-β-cyclodextrin, 30 mM sodium acetate, and 110 mM NaCl, wherein the pH of the composition is 4.5.

Pharmaceutical Composition 45 (PC 45): 0.3 mg/ml nicardipine hydrochloride, 1.8% sulfobutylether-β-cyclodextrin, 30 mM sodium acetate, and 200 mM dextrose, wherein the pH of the composition is 4.5.

Pharmaceutical Composition 46 (PC 46): 0.3 mg/ml nicardipine hydrochloride, 0.75% sulfobutylether-β-cyclodextrin, 30 mM sodium acetate, and 125 mM NaCl, wherein the pH of the composition is 4.5.

Pharmaceutical Composition 47 (PC 47): 0.3 mg/ml nicardipine hydrochloride, 1.0% sulfobutylether-β-cyclodextrin, 30 mM sodium acetate, and 125 mM NaCl, wherein the pH of the composition is 4.5.

Pharmaceutical Composition 48 (PC 48): 0.3 mg/ml nicardipine hydrochloride, 3.4% sorbitol, and 50 mM sodium succinate, wherein the pH of the composition is 5.6.

Pharmaceutical Composition 49 (PC 49): 0.3 mg/ml nicardipine hydrochloride, 1.3% propylene glycol, and 50 mM sodium acetate, wherein the pH of the composition is 5.6.

Pharmaceutical Composition 50 (PC 50): 0.3 mg/ml nicardipine hydrochloride, 1.8% sulfobutylether-β-cyclodextrin, 30 mM sodium acetate, and 110 mM NaCl, wherein the pH of the composition is 5.0.

Pharmaceutical Composition 51 (PC 51): 0.3 mg/ml nicardipine hydrochloride, 0.75% sulfobutylether-β-cyclodextrin, 30 mM sodium acetate, and 125 mM NaCl, wherein the pH of the composition is 4.5.

Pharmaceutical Composition 52 (PC 52): 0.3 mg/ml nicardipine hydrochloride, 1.0% sulfobutylether-β-cyclodextrin, 30 mM sodium acetate, and 125 mM NaCl, wherein the pH of the composition is 4.5.

Pharmaceutical Composition 53 (PC 53): 0.3 mg/ml nicardipine hydrochloride, 0.5% sorbitol, 0.3% propylene glycol, 30 mM sodium acetate, and 90 mM NaCl, wherein the pH of the composition is 5.2.

Pharmaceutical Composition 54 (PC 54): 0.3 mg/ml nicardipine hydrochloride, 1.0% sulfobutylether-β-cyclodextrin, 30 mM sodium acetate, and 125 mM NaCl, wherein the pH of the composition is 4.5.

Pharmaceutical Composition 55 (PC 55): 0.3 mg/ml nicardipine hydrochloride, 0.75% sulfobutylether-3-cyclodextrin, 30 mM sodium acetate, and 125 mM NaCl, wherein the pH of the composition is 4.5.

Pharmaceutical Composition 56 (PC 56): 0.3 mg/ml nicardipine hydrochloride, 0.5% sorbitol, 0.3% propylene glycol, 50 mM sodium acetate, and 90 mM NaCl, wherein the pH of the composition is 5.2.

The excipient concentration in the control formulation (CF) is identical to the commercial product formulation (CPF), CARDENE® I.V (nicardipine hydrochloride ampul). However, the concentration of active ingredient in the commercial and control formulations is different. In the commercial product formulation (CPF), the concentration of nicardipine hydrochloride in the ampul is 2.5 mg/mL before dilution, and 0.1 mg/ml after dilution with appropriate IV fluids before administration. The control formulation (CF), which is designed for premixed ready-to-use intravenous bags such that no further dilution with intravenous fluids is required, has a nicardipine hydrochloride concentration of 0.3 mg/mL. The purpose of the control formulation was to help assess the degradation propensity of the evaluated formulations. Comparable degradation profiles at stressed conditions is indicative of comparable formulation stability.

Example 7

Vial Stability Data with Sorbitol and Propylene Glycol Formulations

The stability in vials of pharmaceutical compositions of the present invention comprising a co-solvent and a buffering agent were compared to the control formulation and the commercial product formulation. Stability was determined by comparing the drug concentration over time for the below compositions. Specifically, the below compositions were prepared according to the method in Example 6:

50 mM Na-acetate, pH 3.5, 4.1% sorbitol (PC 5),
50 mM Na-acetate, pH 3.5, 1.9% propylene glycol (PC 6),
50 mM Na-acetate, pH 4.5, 4.1% sorbitol (PC 7),
50 mM Na-acetate, pH 4.5, 1.8% propylene glycol (PC 8),
50 mM Na-acetate, pH 5.0, 3.7% sorbitol (PC 1),
50 mM Na-acetate, pH 5.0, 1.7% propylene glycol (PC 2),
Control formulation: 0.3 mg/mL, 2.5 mM citrate, 5% sorbitol, pH 3.5 (CF), and
Commercial product formulation: 2.5 mg/ml, 2.5 mM citrate, 5% sorbitol, pH 3.5 (CPF).

These stability studies were performed in 2 ml glass vials and at elevated temperature conditions, in this case 45° C. Formulation stability was monitored by measuring the drug concentration by RP-HPLC against a standard curve. The drug concentration measurements were taken at the start of the experiment, 7 days and 21 days, except for the commercial product formulation, which measurements were taken at the start of the experiment and 46 days. These measurements were then converted into a percentage in order to show the percentage of drug remaining after a period of time.

The data from these stability studies are shown in the below Tables.

| PC # | Drug Conc. (µg/ml) t = 0 | % Drug Remaining | Drug Conc. (µg/ml) t = 7 days | % Drug Remaining | Drug Conc. (µg/ml) t = 21 days | % Drug Remaining |
|---|---|---|---|---|---|---|
| 5 | 314 | 100 | 312 | 99 | 289 | 92 |
| 6 | 302 | 100 | 305 | 101 | 282 | 93 |
| 7 | 304 | 100 | 303 | 100 | 283 | 93 |
| 8 | 304 | 100 | 304 | 100 | 282 | 93 |
| 1 | 298 | 100 | 294 | 98 | 274 | 92 |
| 2 | 290 | 100 | 302 | 104 | 264 | 91 |
| CF | 302 | 100 | 301 | 100 | 277 | 92 |

| PC # | Drug Conc. (µg/ml) t = 0 | % Drug Remaining | Drug Conc. (µg/ml) t = 46 days | % DRUG Remaining |
|---|---|---|---|---|
| CPF | 2553 | 100 | 2265 | 89 |

The data show that the stability in vials, drug concentration over time, of the pharmaceutical compositions of the present invention that contain co-solvents are comparable to both the control formulation (CF) and the current product formulation (CPF). In addition, the compositions had no additional degradation products relative to the control formulation (data not shown).

Example 8

Vial Stability Data with SBEBCD Formulations

The stability in vials of pharmaceutical compositions of the present invention comprising a complexing agent and a buffering agent were compared to the control formulation and the commercial product formulation. Stability was determined by comparing the drug concentration over time for the below compositions. Specifically, the below compositions were prepared according to the method in Example 6:

50 mM Na-acetate, 8.5% SBE-beta cyclodextrin, pH 5.0 (PC 13),
50 mM Na-citrate, 8.5% SBE-beta cyclodextrin, pH 5.5 (PC 14),
50 mM Na-succinate, 8.5% SBE-beta cyclodextrin, pH 5.5 (PC 11), 50 mM Na-succinate, 8.5% SBE-beta cyclodextrin, pH 6.0 (PC 12), Control formulation: 0.3 mg/mL, 2.5 mM citrate, 5% sorbitol, pH 3.5 (CF), and Commercial product formulation: 2.5 mg/ml, 2.5 mM citrate, 5% sorbitol, pH 3.5 (CPF).

These stability studies were performed in 2 ml glass vials and at elevated temperature conditions, in this case 45° C. Formulation stability was monitored by measuring the drug concentration by RP-HPLC against a standard curve. The drug concentration measurements were taken at the start of the experiment, 6 days, 13 days and 30 days, except for the commercial product formulation, which measurements were taken at the start of the experiment and 46 days. These measurements were then converted into a percentage in order to show a percentage of drug remaining after a period of time.

The data from these stability studies are shown in the following Tables.

| PC # | [Drug] (μg/ml) t = 0 | % Drug Remaining | [Drug] (μg/ml) t = 6 d | % Drug Remaining | [Drug] (μg/ml) t = 13 d | % Drug Remaining | [Drug] (μg/ml) t = 30 d | % Drug Remaining |
|---|---|---|---|---|---|---|---|---|
| 13 | 381 | 100 | 387 | 101 | 413 | 108 | 390 | 102 |
| 14 | 334 | 100 | 339 | 101 | 352 | 105 | 333 | 100 |
| 11 | 364 | 100 | 378 | 104 | 396 | 109 | 364 | 100 |
| 12 | 318 | 100 | 341 | 107 | 355 | 112 | 326 | 103 |
| CF | 339 | 100 | 352 | 104 | 363 | 107 | 338 | 100 |

| PC # | Drug Conc. (μg/ml) t = 0 | % Drug Remaining | Drug Conc. (μg/ml) t = 46 days | % Drug Remaining |
|---|---|---|---|---|
| CPF | 2553 | 100 | 2265 | 89 |

The data show that the stability in vials, drug concentration over time, of the pharmaceutical compositions of the present invention that contain SBEBCD are comparable to both the control formulation (CF) and the commercial product formulation (CPF). In addition, the compositions had no additional degradation products relative to the control formulation (data not shown). It is also worth noting that the target concentration of 0.2-0.3 mg/mL could be readily attained in the presence of sulfobutylether-β-cyclodextrin.

Example 9

Intravenous Bag Stability Data with Sorbitol and Propylene Glycol Formulations

The stability in intravenous bags of pharmaceutical compositions of the present invention comprising a co-solvent and a buffering agent were compared to a control formulation. Stability was determined by comparing the drug concentration over time for the below compositions. Specifically, the below compositions were prepared according to the method in Example 6:

50 mM Na-acetate, pH 3.5, 4.1% sorbitol (PC 5), 50 mM Na-acetate, pH 3.5, 1.9% propylene glycol (PC 6), and Control formulation: 0.3 mg/mL, 2.5 mM citrate, 5% sorbitol, pH 3.5 (CF).

These stability studies were performed in 50 ml intravenous bags and at elevated temperature conditions, in this case 45° C. Formulation stability was monitored by measuring the drug concentration by RP-HPLC against a standard curve. The drug concentration measurements were taken at the start of the experiment, 7 days and 21 days. These measurements were then converted into a percentage in order to show the percentage of drug remaining after a period of time.

The data from these stability studies are shown in the Table below.

| PC # | Drug Conc. (μg/ml) t = 0 | % Drug Remaining | Drug Conc. (μg/ml) t = 7 days | % Drug Remaining | Drug Conc. (μg/ml) t = 21 days | % Drug Remaining |
|---|---|---|---|---|---|---|
| 5 | 314 | 100 | 317 | 101 | 319 | 102 |
| 6 | 302 | 100 | 311 | 103 | 297 | 98 |
| CF | 302 | 100 | 276 | 92 | 264 | 88 |

The data show that the stability in intravenous bags, drug concentration over time, of the pharmaceutical compositions of the present invention that contain co-solvents are comparable to the control formulation. In addition, the compositions had no additional degradation products relative to the control formulation (data not shown). Finally, drug adsorption on the bag surface was minimal at pH 3.5.

Example 10

Intravenous Bag Stability Data with HPCD Formulations

The stability of a pharmaceutical composition of the present invention comprising a complexing agent and a buffering agent was evaluated in both vials and intravenous bags. Stability was determined by comparing the drug concentration over time for the below composition. Specifically, the below composition was prepared according to the method in Example 6:

50 mM Na-acetate, pH 5.0, 22.5% HPCD (PC 15).

These stability studies were performed in 50 ml intravenous bags and at elevated temperature conditions, in this case 45° C. The stability evaluations were done with a 10 mL fill volume in both the upright and inverted bag configurations. These evaluations were done relative to the same formulation in a 2 mL glass vial, as a control. Formulation stability was monitored by measuring the drug concentration by RP-HPLC against a standard curve. The drug concentration measurements were taken at the start of the experiment, 1 day, 2 days, 6 days, 9 days and 16 days.

The data from these stability studies are shown in the Table below.

|  | Drug Conc. (µg/ml) t = 0 | Drug Conc. (µg/ml) t = 1 day | Drug Conc. (µg/ml) t = 2 days | Drug Conc. (µg/ml) t = 6 days | Drug Conc. (µg/ml) t = 9 days | Drug Conc. (µg/ml) t = 16 days |
| --- | --- | --- | --- | --- | --- | --- |
| Vial | 271 | 271 | 263 | 260 | 269 | 274 |
| Upright Bag | 271 | 266 | 244 | 264 | 270 | 301 |
| Inverted Bag | 271 | 233 | 203 | 175 | 172 | 150 |

The data show that the stability, drug concentration over time, of the pharmaceutical composition of the present invention that contains complexing agent is more promising in the upright configuration of the bag. The data also show that the recovery of drug product was poorer in the inverted bag configuration.

In order to determine why the composition was more stable in upright intravenous bags compared to inverted intravenous bags, additional experiments were conducted. The drop in drug concentration was not due to any new degradation product (data not shown). We believe that the drop in drug concentration was due to drug adsorption on the bag surface. For many hydrophobic drugs, adsorption on PVC surfaces is a commonly reported concern. Therefore, it is likely that we observed significant adsorption in the inverted configuration because the drug is in contact with PVC surfaces. These results suggest the use of non-PVC bags and/or the careful evaluation of the bag size (solution volume) as feasible options to minimize drug adsorption in order to achieve adequate drug product recovery.

Example 11

Intravenous Bag Stability Data with Sorbitol Formulations

The stability of a pharmaceutical composition of the present invention comprising a cosolvent and a buffering agent was evaluated in both vials and intravenous bags. Stability was determined by comparing the drug concentration over time for the below composition. Specifically, the below composition was prepared according to the method in Example 6:

50 mM Na-acetate, pH 5.0, 3.7% sorbitol (PC 1).

These stability studies were performed in 50 ml intravenous bags and at elevated temperature conditions, in this case 45° C. The stability evaluations were done with both 10 and 50 mL fill volumes in both the upright and inverted bag configurations. These evaluations were done relative to the same formulation in a 2 mL glass vial, as a control. Formulation stability was monitored by measuring the drug concentration by RP-HPLC against a standard curve. The drug concentration measurements were taken at the start of the experiment, 1 day, 2 days, 5 days, 9 days and 16 days.

The data from these stability studies are shown in the below Table.

|  | Drug Conc. (µg/ml) t = 0 | Drug Conc. (µg/ml) t = 1 day | Drug Conc. (µg/ml) t = 2 days | Drug Conc. (µg/ml) t = 6 days | Drug Conc. (µg/ml) t = 9 days | Drug Conc. (µg/ml) t = 16 days |
| --- | --- | --- | --- | --- | --- | --- |
| Vial | 100 | 102 | 100 | 110 | 104 | 106 |
| Upright Bag 10 ml | 100 | 93 | 89 | 98 | 85 | 87 |
| Upright Bag 50 ml | 100 | 98 | 96 | 114 | 97 | 98 |
| Inverted Bag 10 ml | 100 | 46 | 43 | 38 | 21 | 13 |
| Inverted Bag 50 ml | 100 | 89 | 87 | 102 | 86 | 85 |

The data show that the stability, drug concentration over time, of the pharmaceutical composition of the present invention that contains cosolvent is more promising in the upright configuration of the bag. The data also show that the recovery of drug product was poorer in the inverted bag configuration.

In order to determine why the composition was more stable in upright intravenous bags compared to inverted intravenous bags, additional experiments were conducted. The drop in drug concentration was not due to any new degradation product (data not shown). We believe that the drop in drug concentration was due to drug adsorption on the bag surface. For many hydrophobic drugs, adsorption on PVC surfaces is a commonly reported concern. Therefore, it is likely that we observed significant adsorption in the inverted configuration because the drug is in contact with PVC surfaces. This belief is further supported by the fact that we observed poorer recovery of the drug in the 10 mL fill configuration relative to the 50 mL fill configuration, although this poorer recovery may be partly due to the fact that the 10 mL fill configuration has a higher surface area to volume ratio, which adversely impacts drug adsorption and recovery. In conclusion, these results suggest the use of non-PVC bags and/or the careful evaluation of the bag size (solution volume) as feasible options to minimize drug adsorption in order to achieve adequate drug product recovery.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. Any conflict between any reference cited herein and the specific teachings of this specification shall be resolved in favor of the latter.

What is claimed is:

1. A pharmaceutical composition comprising an aqueous solution comprising an inclusion complex of nicardipine or a pharmaceutically acceptable salt thereof, a buffering agent and a sulfoalkylated β-cyclodextrin,
   wherein the composition is premixed and is formulated for direct parenteral bolus administration for immediate use without dilution to a human subject, and wherein a pH of the composition is 4.5 to 5.5,
   wherein the composition is in unit dose format and the unit dose contains the formulation in a volume of from 0.5 to 20 ml,
   wherein the nicardipine concentration is 0.5 mg/ml, and
   wherein the sulfoalkylated β-cyclodextrin in the pharmaceutical composition is from 2% to 5% (w/v) wherein the sulfoalkylated β-cyclodextrin is a sulfobutylated β-cyclodextrin having an average of 5 to 8 degrees of sulfobutylation.

2. The pharmaceutical composition of claim 1, wherein the sulfobutylated β-cyclodextrin is sulfobutylether β-cyclodextrin.

3. The pharmaceutical composition of claim 1, wherein the pharmaceutically acceptable salt of nicardipine is the nicardipine hydrochloride salt.

4. The pharmaceutical composition of claim 1, comprising the pharmaceutically acceptable salt of nicardipine in a parenterally injectable aqueous carrier, wherein the concentration of the buffering agent in the composition is 0.1 mM to 100 mM.

5. The pharmaceutical composition of claim 4, wherein the sulfoalkylated β-cyclodextrin is a sulfobutylated β-cyclodextrin having an average of 7 degrees of sulfobutylation.

6. The pharmaceutical composition of claim 4, wherein the buffering agent comprises at least one agent selected from a group consisting of acetate, citrate, succinate, and phosphate.

7. The pharmaceutical composition of claim 4, further comprising a tonicity adjusting agent.

8. The pharmaceutical composition of claim 4, wherein the composition further comprises at least one co-solvent in a concentration of 0.1 to 25% (w/v).

9. The pharmaceutical composition of claim 8, wherein concentration of at least one co-solvent is 0.1 to 10% (w/v).

10. The pharmaceutical composition of claim 4, wherein the pH is above a pH of 4.5 and equal to or less than a pH of 5.5.

* * * * *